(12) United States Patent
Miyazaki et al.

(10) Patent No.: US 6,801,800 B2
(45) Date of Patent: Oct. 5, 2004

(54) MR IMAGING USING ECG-PREP SCAN

(75) Inventors: Mitsue Miyazaki, Otawara (JP); Satoshi Sugiura, Otawara (JP)

(73) Assignee: Kabushiki Kaisha Toshiba, Kanagawa-Ken (JP)

( * ) Notice: Subject to any disclaimer, the term of this patent is extended or adjusted under 35 U.S.C. 154(b) by 232 days.

(21) Appl. No.: 09/773,380

(22) Filed: Feb. 1, 2001

(65) Prior Publication Data

US 2002/0032376 A1 Mar. 14, 2002

(30) Foreign Application Priority Data

Dec. 27, 2000 (JP) ........................................ 2000-399259

(51) Int. Cl.$^7$ ................................................ A61B 5/05
(52) U.S. Cl. .................. 600/410; 600/407; 600/413; 600/419; 600/436; 606/2; 606/20; 606/27; 606/32; 324/306; 324/307; 324/309; 128/653.2; 128/653.5
(58) Field of Search ................................ 600/407, 410, 600/413, 419, 436, 508, 513, 522, 529, 523, 481, 504, 408, 411, 428, 425; 606/2–32; 128/653.2, 653.5; 324/300, 306, 307, 309, 318; 382/128, 130, 131, 280, 276; 524/300, 307–312, 306

(56) References Cited

U.S. PATENT DOCUMENTS

| | | | | | |
|---|---|---|---|---|---|
| 4,609,872 | A | * | 9/1986 | O'Donnell | 324/306 |
| 4,752,734 | A | * | 6/1988 | Wedeen | 324/306 |
| 4,995,394 | A | * | 2/1991 | Cline et al. | 600/410 |
| 5,101,156 | A | * | 3/1992 | Pelc | 324/306 |
| 5,122,747 | A | * | 6/1992 | Riederer et al. | 324/309 |
| 5,221,898 | A | * | 6/1993 | Takiguchi et al. | 324/306 |

(List continued on next page.)

FOREIGN PATENT DOCUMENTS

| | | |
|---|---|---|
| JP | 2-43494 | 9/1990 |
| JP | 3-53936 | 8/1991 |
| JP | 11-239571 | 9/1999 |
| JP | 2000-300538 | 10/2000 |

OTHER PUBLICATIONS

Prince, "Gadolinium–Enhanced MR Aortography", RADIOGRAPHY 1994, 191; 155–164.

Kim et al, "3–D MR Angiography with Scanning 2–D Images—Simultaneous Data Acquisition of Arteries and Veins (SAAV)", Magnetic Resonance in Medicine 14, 554–561 (1990).

Miyazaki et al, "Non–Contrast–Enhanced MR Angiography Using 3D ECG–Synchronized Half–Fourier Fast Spin Echo", Journal of Magnetic Resonance Imaging 12:776–783 (2000).

Chung et al, "Inversion Recovery Cine TruFISP for Optimizing TI in Myocardinal Infarct Imaging", Proc. Intl. Soc. Mag. Reson, Med. 10 (2002).

Primary Examiner—Angela D. Sykes
Assistant Examiner—William C Jung
(74) Attorney, Agent, or Firm—Nixon & Vanderhye P.C.

(57) ABSTRACT

An ECG-prep scan is used to set an optimum time phase in both systole and diastole of the heart. At each of the different time phases, an imaging scan is started to acquire a plurality of sets of echo data. An artery/vein visually separated blood flow image is produced from the echo data. The imaging scan uses a half-Fourier technique, for example. This provides high-quality blood flow images with shorter scan time, without injecting a contrast medium. Additionally, with a readout gradient pulse applied substantially parallel with a direction of slowly flowing blood, a scan is performed in synchronism with an optimally determined cardiac time phase. The readout gradient pulse has a dephasing pulse for enhancing differences in a flow void effect depending on blood flow velocities. This enables slow-speed flows, such as blood flows in the inferior limb, to be depicted without fail.

45 Claims, 26 Drawing Sheets

U.S. PATENT DOCUMENTS

| | | | | |
|---|---|---|---|---|
| 5,320,099 A | * | 6/1994 | Roberts et al. | 324/306 |
| 5,417,214 A | * | 5/1995 | Roberts et al. | 324/306 |
| 5,519,320 A | * | 5/1996 | Kanayama et al. | 324/309 |
| 5,565,776 A | * | 10/1996 | Kanazawa | 324/306 |
| 5,565,777 A | * | 10/1996 | Kanayama et al. | 324/309 |
| 5,830,143 A | * | 11/1998 | Mistretta et al. | 324/306 |
| 5,910,728 A | * | 6/1999 | Sodickson | 324/309 |
| 6,043,655 A | * | 3/2000 | Makita et al. | 324/307 |
| 6,144,201 A | * | 11/2000 | Miyazaki | 324/306 |
| 6,320,377 B1 | * | 11/2001 | Miyazaki et al. | 324/306 |
| 6,353,752 B1 | * | 3/2002 | Madore et al. | 600/410 |

* cited by examiner

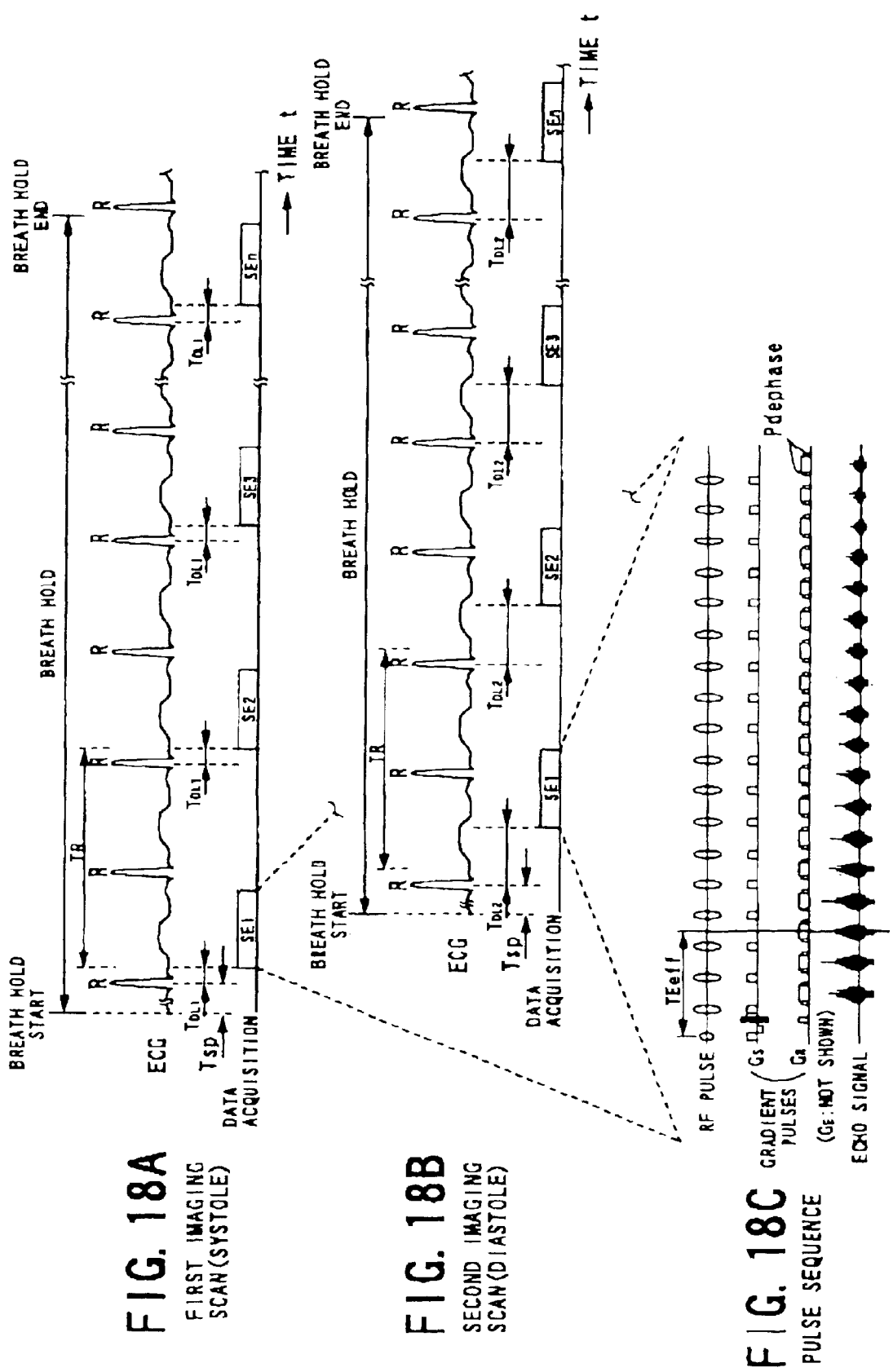
FIG. 18A FIRST IMAGING SCAN (SYSTOLE)
FIG. 18B SECOND IMAGING SCAN (DIASTOLE)
FIG. 18C PULSE SEQUENCE

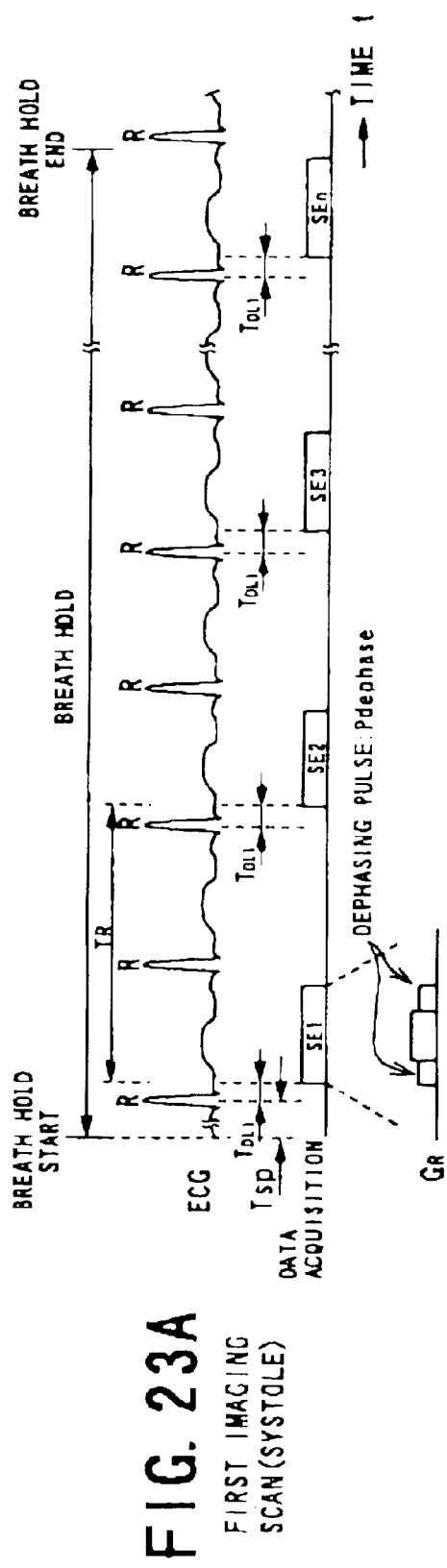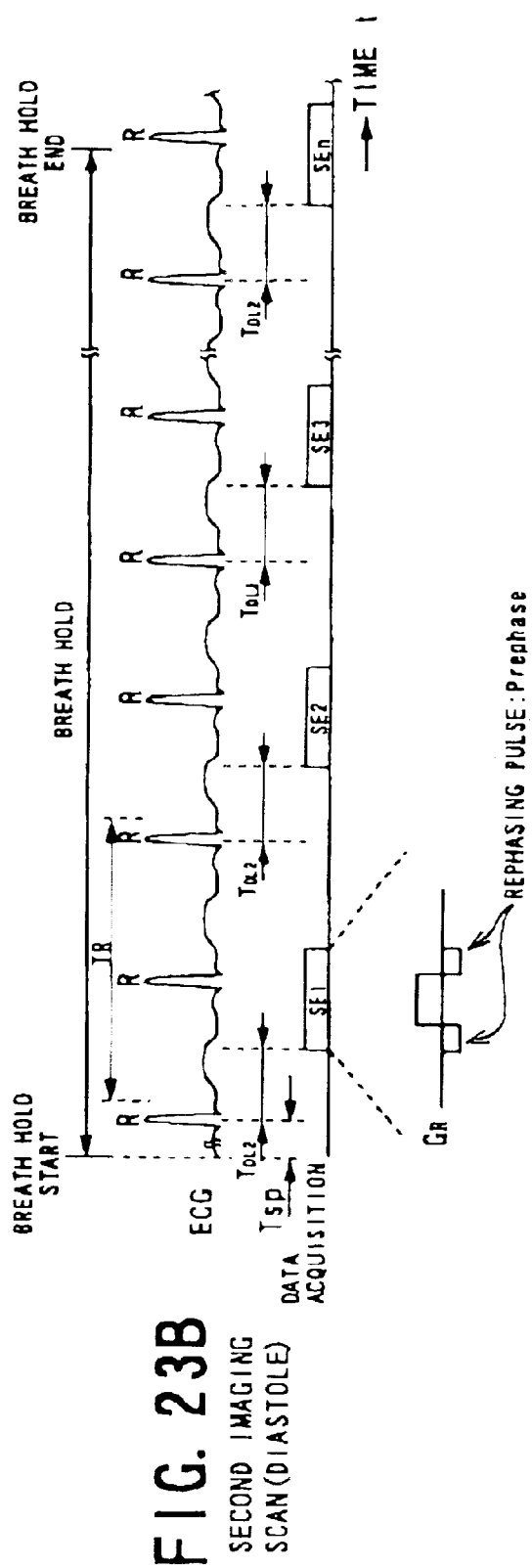

MR IMAGING USING ECG-PREP SCAN

BACKGROUND OF THE INVENTION

1. Field of the Invention

The present invention relates to magnetic resonance imaging (MRI) for internally imaging an object to be examined on the basis of a magnetic resonance phenomenon of nuclear spins of the object, particularly, to an MRI (magnetic resonance imaging) system and an MR (magnetic resonance) method capable of acquiring artery/vein visually separated images of the object without using a contrast medium.

2. Description of the Related Art

Magnetic resonance imaging is based on an imaging technique for magnetically exciting nuclear spins of an object located in a static magnetic field by applying a radio-frequency (RF) signal of a Larmor frequency and reconstructing an image from MR signals induced by the excitation.

For clinically obtaining blood flow images of the pulmonary field or abdomen of a patient by magnetic resonance imaging, MR angiography has been put in practical use, in which a contrast medium is injected into the object to highlight blood flows. However, this contrast MR angiography needs an invasive treatment to inject the contrast medium. First of all, mental and physical burdens on patients become large. Second, examination cost of the contrast MR angiography is still expensive. Third, there are some cases where a contrast medium cannot be injected into patients due to patient's physical characteristics.

In cases the contrast medium cannot be injected or is not used, imaging techniques, such as time-of-flight (TOF) and phase contrast (PC) techniques are used alternatively.

The time-of-flight method and phase contrast techniques utilize an effect of flows such as blood flows. The effect of flows is attributed to either of two natures possessed by spins in motion. One is that spins simply move their positions due to flows, while the other results from phase shifts of transverse magnetization caused when spins move in a gradient field. The nature of the position movement is used for the TOF technique and the nature of the phase shifts is used for the phase contrast technique.

However, when the TOF technique or phase contrast technique is used for obtaining MR images of a patient's pulmonary field or abdomen which depict flows of large vessels, such as the aorta, in their superior-inferior directions, it is required to scan slices located vertically to the flowing direction. That is, axial images should be acquired with a slice direction of those axial images set to the superior-inferior direction. Thus, in the case that two-dimensional slice imaging is performed to acquire such axial images, it is impossible to obtain an image in which blood flows are directly reflected. Three-dimensional image data spatially containing blood flows are therefore needed, but the number of slices increases which will cause an entire imaging time to be longer.

A novel MR imaging technique, known as an FBI (Fresh Blood Imaging) technique, has been proposed to overcome the foregoing inconveniences. In MR imaging on the FBI technique, an optimum time delayed from an R-wave of an ECG signal is predetermined, and ECG-synchronized MR scanning is performed at the delay time, thus well tracing a fresh and stable high-velocity blood flow ejected from the heart every appearance of the R-wave. In the FBI technique, three-dimensional scanning is additionally performed under the condition that signal intensities from parenchyma are actively suppressed by employing imaging conditions that include setting of a shorter repetition time TR (this causes the longitudinal relaxation time of parenchyma at rest to be insufficient) and applying an IR (Inversion Recovery) pulse or fat-suppression pulse (i.e., suppressing signals to be emanated from fat), thereby the blood flow being depicted. This eliminates the necessity of using a contrast medium, and blood flow images can be provided within a relatively shorter scan time.

For obtaining artery/vein visually separated blood flow images by using the FBI technique, a three-dimensional scan should be performed two times at different ECG-synchronized timings, and two sets of three-dimensional echo data acquired by the two-time three-dimensional scans or two sets of three-dimensional image data individually formed from the two sets of three-dimensional echo data should undergo weighted subtraction between the two sets of data.

In other words, even when the FBI technique is used, there remain some drawbacks that should be resolved. One drawback is that a longer scan time is still needed in total, because a three-dimensional scan should be performed two times. Another is that registration may be mistaken if the position of a patient's body moves between two times of scans, which is apt to deteriorate quality of blood flow images which will be produced by the subtraction.

On the other hand, the foregoing TOF and phase contrast techniques are based on the effect of flows of fluid such as blood. Although depending on the characteristics of an MRI system, it is general that either of the TOF or phase contrast method depicts only blood flows whose flowing speed is 2 to 3 cm/s or more. Blood flowing slower than this speed is scarcely detected. For example, peripheral veins, lymphatic vessels, CSF (cerebrospinal fluid), pancreatic duct, and others of a patient (human being) are slower in flow speed, and their flow speeds are approximately 1 cm/s or lower in general. Additionally, there may occur influence of positional shifts due to heartbeats, it was almost impossible to detect such slower-speed fluid flows by the conventional techniques.

SUMMARY OF THE INVENTION

The present invention has been made to break through the foregoing current situations. A first object of the present invention is to, therefore, provide an MR imaging technique for producing high-quality blood flow images in a shorter scan time, without using a contrast medium.

A second object of the present invention is to provide an MR imaging technique, in addition to the above first object, which is capable of obtaining different types of blood flow images from echo data acquired by the same scanning, thus enriching pieces of information to be provided about blood flows.

A third object of the present invention is to depict such slower-speed flows as peripheral blood flows in a steady manner, with no contrast medium injected.

A fourth object of the present invention is to depict such slower-speed flows as peripheral blood flows in a shorter period of time in a steady and high-quality manner, with no contrast medium injected.

In order to accomplish the above first and second objects, by an MRI system and an MR imaging method according to one aspect of the present invention, a plurality of different cardiac time phases of an object are set, an MR imaging scan is performed to start at the thus-set plural different time phases so that a plurality of sets of echo data are acquired successively, and a blood flow image is produced from the plurality of sets of echo data.

Preferably, the plural different time phases are two time phases falling into the systole and diastole of one cardiac cycle of the object. Still preferably, in the scan, a first scan which starts at the time phase present in the systole and a second scan which starts at the time phase present in the diastole are performed by separated pulse sequences toward the same slice of the object or the same slice encoding for the object.

Still preferably, echo data or image data thereof resultant from the first scan and echo data or image data thereof resultant from the second scan are subject to mutual subtraction, thereby producing echo data or image data thereof repenting an arterial phase image. For example, the subtraction is weighted subtraction.

Further, one example of setting time phases is directed to detection of a signal indicative of the cardiac time phases of the object. A preparing MR sequence is performed on a region to be imaged at each of different times from cyclically-appearing heartbeat reference waves of the detected signal, a plurality of times in total, so that a plurality of frames of MR images are obtained. From the plurality of frames of MR images thus obtained, two cardiac time phases, i.e., two timings in a cardiac cycle are determined. For example, the signal indicative of the cardiac time phase is an ECG signal of the object and the heartbeat reference wave is R-waves of the ECG signal.

This provides higher-quality blood flow images in a shorter scan time, without injection of a contrast medium. Moreover, from echo data acquired in the same imaging, blood flow images such as an arterial phase image and a venous phase image, which are different in types, can be produced in a simple manner. It is therefore possible to enrich blood flow information that can be provided through one time of imaging.

Additionally, in order to accomplish the foregoing third and fourth objects, another aspect of the present invention provides an MRI system and an MR imaging method, in which a scan is performed for an object placed in a static magnetic field, using a pulse sequence including a readout gradient pulse. For performing this scan, a cardiac time phase of the object is set, and the readout gradient pulse is applied to the object in a manner that its applied direction is substantially parallel to a flowing direction of blood in the object. In these states, the scan is performed in synchronism with the cardiac time phase that has been set, with echo signals acquired. An image of either a blood flow or a parenchymal region influenced by the blood flow is produced from the echo signals.

Preferably, the readout gradient pulse has a main pulse to read out an echo signal and a control pulse, which is added to the main pulse, to control behaviors of phase of magnetic spins present in blood. For instance, the control pulse is a pulse to dephase or rephase magnetic spins. By way of example, the cardiac time phase to be set is two in total, one for a systole and one for a diastole. At each of the two cardiac time phases, the scan is performed, so that data consisting of two sets of echo signals are acquired.

Since an applied direction of the readout gradient pulse is almost made to agree with a flowing direction of blood and a dephasing or rephasing pulse is added to the readout gradient pulse, a slower-speed flow, such as blood flows in an inferior limb, can be depicted with accuracy, without using a contrast medium. Particularly, a high-quality image in which arteries and veins are visually separated can be depicted within a short period of time.

BRIEF DESCRIPTION OF THE DRAWINGS

In the accompanying drawings:

FIGS. 18A to 18C are timing charts showing timing of the imaging scan based on an electrocardiogram-synchronized technique in the second embodiment;

FIGS. 23A and 23B are pulse sequences for two times of imaging scans performed as a modification of the second embodiment;

DETAILED DESCRIPTION OF THE PREFERRED EMBODIMENTS

Hereinafter, embodiments of the present invention will be explained.

(1) First Embodiment

Refereeing to FIGS. 1 to 14, a first embodiment will now be described.

(1.1) Configuration of System

Figure 1:
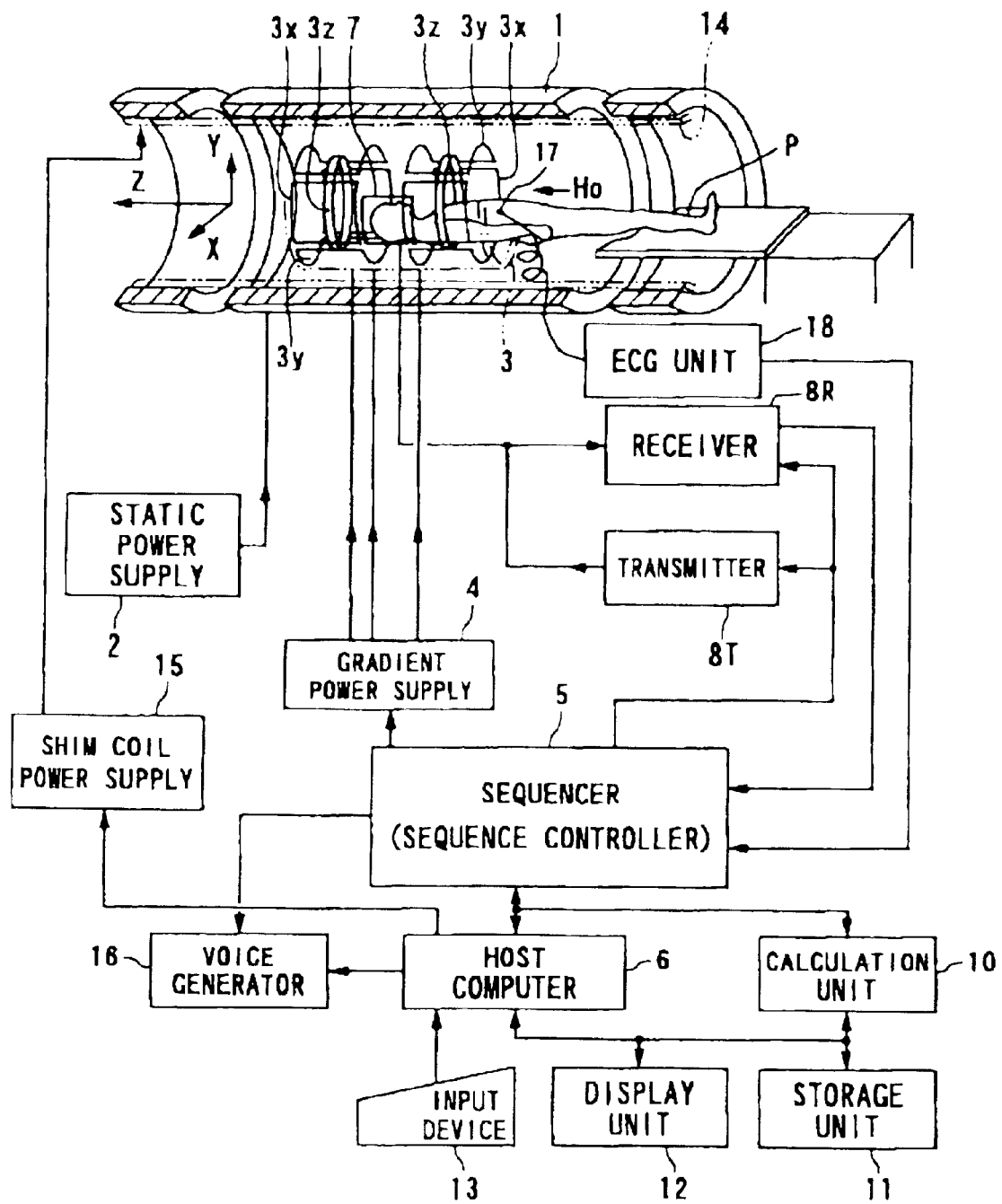
FIG. 1 is a functional block diagram exemplifying the configuration of an MRI system according to embodiments of the present invention.

FIG. 1 shows an outlined hardware configuration of an MRI (magnetic resonance imaging) system used in common in each of the following embodiments.

The MRI system comprises a patient couch on which a patient P lies down, static magnetic field generating components for generating a static magnetic field, magnetic field gradient generating components for appending positional information to a static magnetic field, transmitting/receiving components for transmitting and receiving radio-frequency signals, control and operation components responsible for controlling the whole system and reconstructing images, and electrocardiogram components for acquiring an ECG signal of a patient, the ECG signal being employed as a signal indicative of cardiac time phases of the patient.

The static magnetic field generating components include a magnet 1 that is of, for example, a superconducting type and a static power supply 2 for supplying current to the magnet 1, and generates a static magnetic field $H_0$ in an axial direction (Z-axis direction) in a cylindrical bore (diagnostic space) into which a patient P is inserted. The magnet unit includes shim coils 14. Current used to homogenize the static magnetic field is supplied from a shim coil power supply 15 to the shim coils 14 under the control of a host computer to be described later. The couch top of the patient couch on which the patient P lies down can be inserted into the bore of the magnet 1 so that the couch top can be withdrawn.

The magnetic field gradient generating components includes a gradient coil unit 3 incorporated in the magnet 1. The gradient coil unit 3 includes three pairs (kinds) of x-, y- and z-coils $3x$ to $3z$ used to generate magnetic field gradients changing in strength in X-axis, Y-axis, and Z-axis directions that are mutually orthogonal. The magnetic field gradient generating components further includes a gradient power supply 4 for supplying currents to the x-, y-, and z-coils $3x$ to $3z$. The gradient power supply 4 supplies pulsated currents used to generate magnetic field gradients to the x-, y-, and z-coils $3x$ to $3z$ under the control of a sequencer that will be described later.

The pulsated currents supplied from the gradient power supply 4 to the x-, y-, and z-coils $3x$ to $3z$ are controlled, whereby magnetic field gradients changing in the three X-, Y-, and Z-directions (physical axis directions) are synthesized. Thus, a magnetic field gradient $O_s$ in a slice direction, a magnetic field gradient $G_E$ in a phase-encode direction, and a magnetic field gradient $G_R$ in a read-out direction (frequency-encoding direction), which are mutually orthogonal and logic axis directions, can be specified and changed arbitrarily. The gradients generated in the slice, phase-encode, and read-out directions are superposed on the static magnetic field $H_0$.

The transmitting/receiving components includes an RF coil 7 located in the vicinity of a patient P in the diagnostic space inside the magnet 1, and a transmitter 8T and a receiver 8R both connected to the coil 7. The transmitter 8T and receiver 8R operate under the control of a sequencer 5 described later. The transmitter 8T supplies to the RF coil 7 RF current pulses of a Larmor frequency, which are used to induce the nuclear magnetic resonance (NMR). The receiver 8R takes in MR signals (radio-frequency signals) received by the RF coil 7, carries out various kinds of signal processing, such as pre-amplification, intermediate-frequency conversion, phase detection, low-frequency amplification, and filtering, on the echo signals, and carries out an A/D conversion on the processed echo signals so that digital data (original data) of the MR signals are produced.

Furthermore, the control and operation components include a sequencer 5 (also referred to as a sequence controller), host computer 6, calculation unit 10, storage unit 11, display unit 12, input device 13, and voice generator 16. Of them, the host computer 6 provides the sequencer 5 with pulse sequence information and manages the operation of the entire system according to not-shown installed software procedures One feature of the MRI system is that it is able to perform an MR scan based on an electrocardiogram-synchronized technique depending on previously selected one or two synchronization timings (cardiac time phases). In the case that the synchronization timings are two in number, one is set to an optimum time phase residing in a diastole and the other is set to an optimum time phase residing in a systole, respectively.

Figure 2:
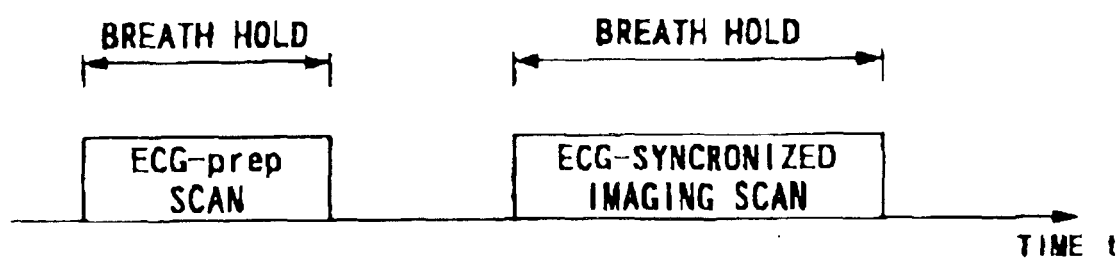
FIG. 2 explains a time-sequential relationship between an ECG-prep scan and an imaging scan in a first embodiment.

In a main program not shown, the host computer 6 performs, as shown in FIG. 2, a preparing scan (hereinafter referred to as an ECG-prep scan) and a scan for imaging (hereinafter referred to as an imaging scan). In the preparing scan, a preparing pulse sequence is executed to decide synchronization timing of one or more time phases. The imaging scan is executed on the basis of an electrocardiogram-synchronized technique that uses the decided synchronization timing. The imaging scan includes scans executed at two time phases, which are repeated on a single repetition time TR. That is, for two-dimensional imaging, echo data for two frames of images are acquired at the two time phases during repetition on the repetition time TR, and for three-dimensional imaging, echo data of two frames are acquired at two time phases during repetition for each slice-encode amount.

Figure 3:
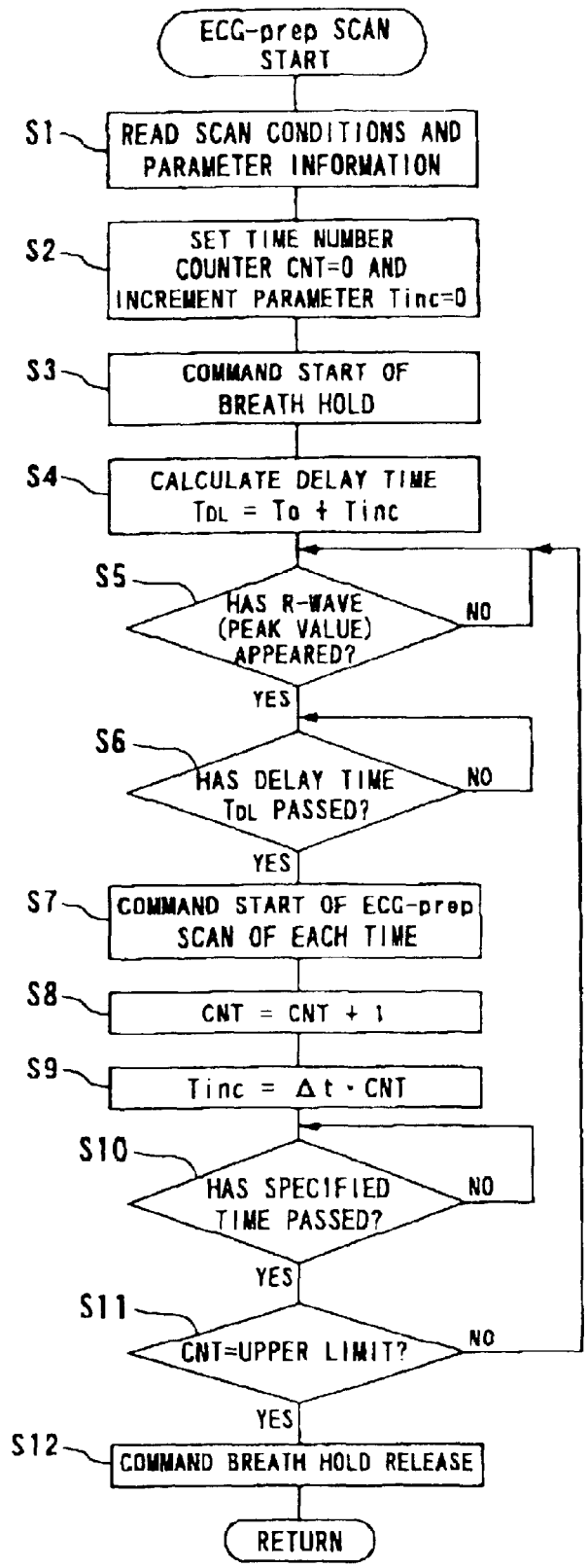
FIG. 3 is an outlined flowchart exemplifying procedures of the ECG-prep scan performed by a host computer.
Figure 6:
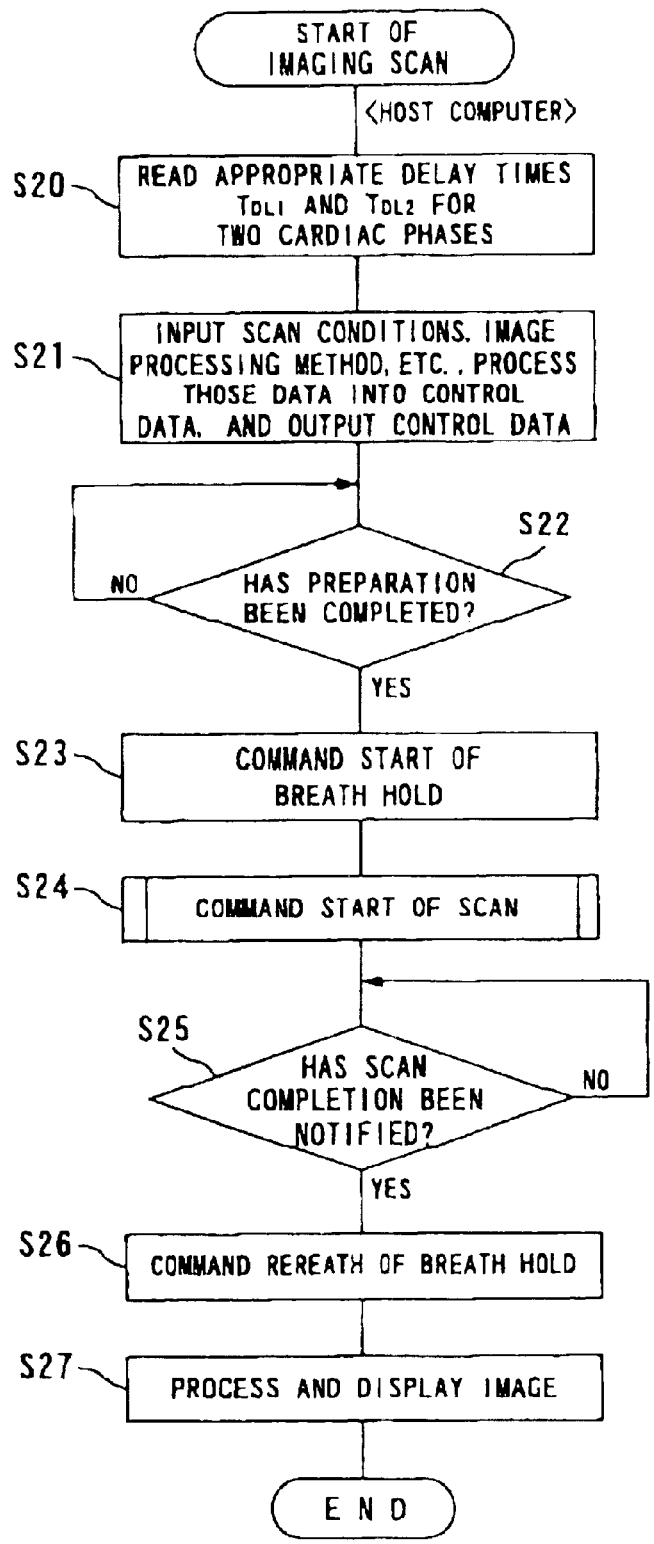
FIG. 6 is an outlined flowchart exemplifying how the imaging scan executed by a host computer is controlled in the first embodiment.
Figure 7:
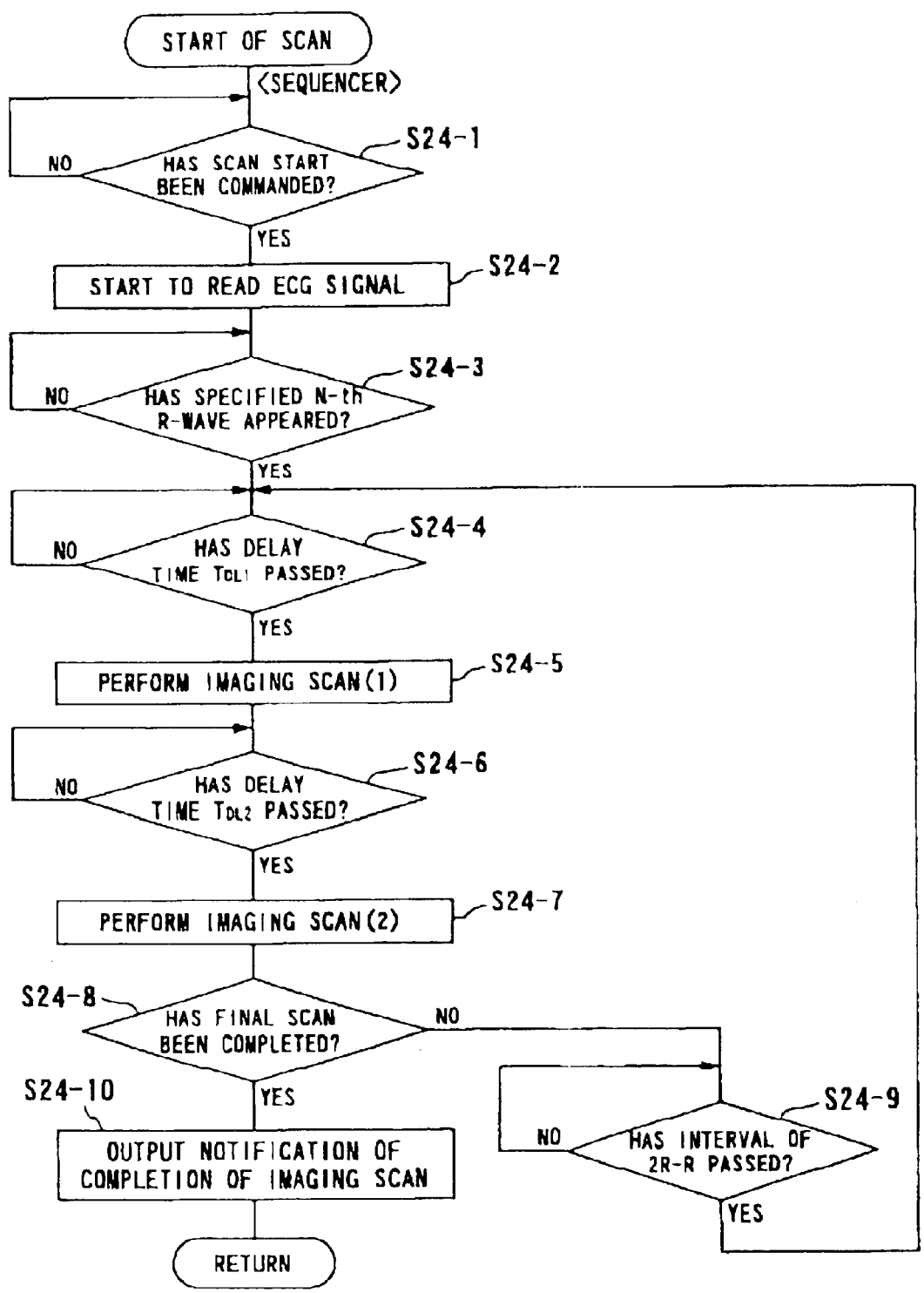
FIG. 7 is an outlined flowchart exemplifying how the imaging scan executed by a sequencer is controlled in the first embodiment.

One execution routine of the ECG-prep scan is exemplified in FIG. 3 and that of the imaging scan based on the electrocardiogram-synchronized technique is exemplified in FIGS. 6 and 7, respectively.

Optimum electrocardiogram synchronization timings are decided through the ECG-prep scan, before a scan for echo data acquisition is executed at the electrocardiogram synchronization timings. This permits blood flow to be traced in a steady manner and fresh blood outputted by the heart to be scanned at any time.

The sequencer 5, which has a CPU and memories, stores pulse-sequence information sent from the host computer 6, controls the operations of the gradient power supply 4, transmitter 8T, and receiver 8R according to the stored information, and temporarily receives digital data corresponding to MR signals outputted from the receiver 8R so as to transmit them to the calculation unit 10. The pulse-sequence information includes all information required for operating the gradient power supply 4, transmitter 8T, and receiver 8R according to a series of pulse sequences. For example, such information includes information about the strength, duration, and application timing of pulsed currents to be applied to the x-, y-, and z-coil 3x to 3z.

As to the pulse sequence, a two-dimensional (2D) scan or three-dimensional (3D) scan can be used, as long as a Fourier transform method is adopted. Particularly, the three-dimensional scan has a greater advantage in shortening a scan time. As pulse trains to those scans, various types of pulse trains based on a fast SE method, EPI (Echo Planar Imaging) method, FASE (Fast Asymmetric SE) method (that is, an imaging technique in which both of the fast SE and half-Fourier methods are combined), and others are available.

The calculation unit 10 receives digital data (also known as original data or raw data) sent from the receiver 8R via the sequencer 5, maps the original data in a Fourier space (also known as a k-space or frequency space) formed in its incorporated memory, and reconstructs the mapped original data into an image in the real space through a two-dimensional or three-dimensional Fourier transform for each set of data. Moreover, the calculation unit performs synthesis and subtraction (weighted subtraction is included) with data of images, according to its necessity. The synthesis includes pixel-by-pixel addition of image data of a plurality of frames and maximum intensity projection (MIP) processing of a plurality of frames of images. Another example of the synthesis is a method by which original data of a plurality of frames are synthesized into a single frame of original data, as they are, with the axes of the frames matched in the Fourier space. Additionally, the addition includes simple addition, averaging, or weighted addition.

The storage unit 11 is able to preserve image data produced by the synthesis or subtraction as well as the reconstructed image data. The display unit 12 displays an image. By using the input device 13, an operator is able to provide with the host computer 6 parameter information for selecting desired synchronization timing, scan conditions, a pulse sequence, and information about processing image synthesis and subtraction.

The voice generator 16 is capable of uttering voice messages informing a patient of the start and end of breath hold in response to instructions sent from the host computer 6.

Furthermore, the electrocardiogram components comprise an ECG sensor 17 attached to a patient body to detect an electric ECG signal and an ECG unit 18 performing various types of processing including digitization with the detected ECG signal and sending it to both the host computer 6 and the sequencer 5. The sequencer 5 uses this measured ECG signal when performing each of the ECG-prep scan and the ECG-synchronized imaging scan. This enables optimum setting of synchronization timing based on the ECG-synchronized method, and data acquisition can be done by the ECG-synchronized imaging scan on the basis of the set synchronization timing.

(1.2) ECG-prep Scan

Figure 4:
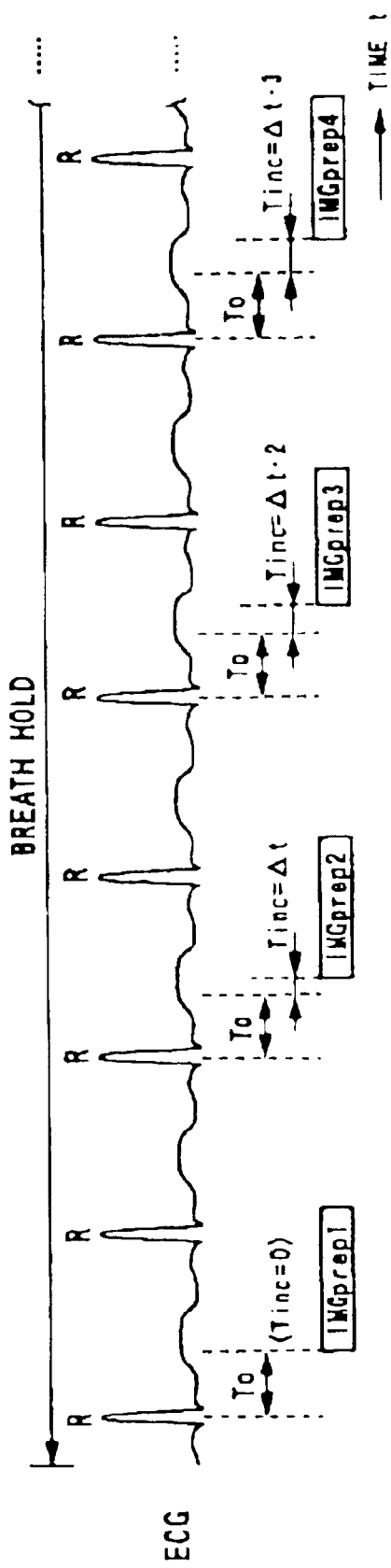
FIG. 4 is a timing chart exemplifying a time-sequential relationship between an ECG signal and the ECG-prep scan.
Figure 5:
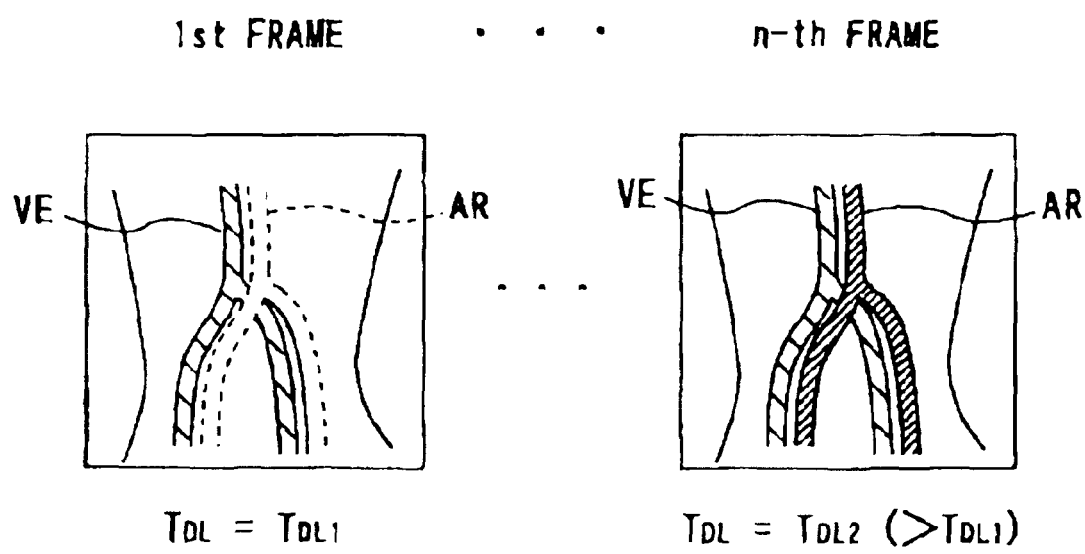
FIG. 5 shows pictorial MRA images obtained by the ECG-prep scan whose delay time is dynamically changed.

Referring to FIGS. 3 to 5, processing for determining a synchronization timing on the ECG-prep scan will now be explained.

The host computer 6, which is in operation for a given main program not shown, responds to a command from the input device 13 and commences to execute an ECG-prep scan shown in FIG. 3.

First, the host computer 6 reads from the input device 13 scan conditions and information about parameters both required to perform the ECG-prep scan (step S1 in the figure). The scan conditions include the type of a scan, the type of a pulse sequence, and a phase-encode direction. The parameter information includes an initial time $T_0$ (herein, defined as an elapsing time from an R-wave peak in the ECG signal) to determine an ECG-synchronized timing (time phase), a time increment $\Delta t$, and an upper limit of a numbering counter CNT. An operator can properly set these parameters.

The initial time $T_0$, time increment $\Delta t$, and the upper limit of the numbering counter CNT are set to amounts so that, for example, a range from a diastole to a systole in a period of "1 R-R" is almost thoroughly covered in time. In the diastole, arterial and venous phases are both depicted, while in the systole, only a venous phase is depicted. By way of example, the initial time $T_0$ may be set to $T_0=0$.

The host computer 6 then initializes the numbering counter CNT counting the execution times of the sequence and a time increment parameter $T_{inc}$ determining the synchronization timing (CNT=0, $T_{inc}$=0; step S2). After this, the host computer 6 sends massage data to the voice generator 16 to generate breath-hold instructions, such as "Hold your breath, please." toward an object (patient) (step S3). It is preferred that the breath hold is performed for suppression of body motions of a patient that may be caused during the ECG-prep scan. However, in some occasions, the ECG-prep scan may be performed with no breath hold After having completed the above preparation, the host computer 6 sequentially executes processes shown after step 4. This execution permits the scan with the ECG-synchronized timing changed.

Specifically, an expression of $T_{DL}=T_0+T_{inc}$ is calculated to obtain a delay time $T_{DL}$ from the peak time instant of an R-wave (step S4) An ECG signal that has experienced the signal processing in the ECO unit 18 is then read, and it is determined whether or not the R-wave peak value has appeared in the signal (step S5). This determination will be repeated until the R-wave appears. When the R-wave appears (Yes at step S5), it is then determined whether or not the delay time $T_{DL}$ calculated at step S4 has elapsed since the appearance of the R-wave peak time (step S6). This determination will also be repeated until the delay time $T_{DL}$ elapses.

When the time has passed by the delay time $T_{DL}$ since the R-wave peak time instant (Yes at step S6), the sequencer 5 is ordered to start a pulse sequence of each time (step S7, refer to FIG. 4). It is preferred that this pulse sequence is identical in type to the imaging pulse sequence later described. For example, an available pulse sequence is based on the 2D-FASE (Fast Asymmetric SE) technique combining the fast SE method and the half-Fourier method. Of course, a variety of other pulse sequences, such as a fast SE method and an EPI method, are usable for this pulse sequence. In response to the instructions, the sequencer 5 commences performing an operator-specified type of pulse sequence, resulting in that a region of a desired portion in the object is scanned. In the event that, for example, the imaging scan (main scan) for image data acquisition is performed on a three-dimensional (3D) technique, the ECG-prep scan may be either a two-dimensional scan or a three-dimensional scan whose scan region is made to agree with that for the imaging scan. In the embodiment, the imaging scan is performed as a three-dimensional scan, while the ECG-prep scan is performed as a two-dimensional scan with consideration of a shortened scan time. In light of an object of the ECG-prep scan, the two-dimensional scan is still enough for the ECG-prep scan.

After the above sequence has been instructed to start, the numbering counter CNT is incremented such that CNT=CNT+1 (step S8), then the time increment parameter $T_{inc}$ is computed such that $T_{inc}=\Delta T \times CNT$ (step S9). In other words, every time when the pulse sequence is ordered to be executed, the count of the counter CNT increases by one and the increment parameter $T_{inc}$ for adjusting the synchronization timing increases in proportion to the count.

Then, a standby state continues until a period of predetermined time (for example, approx. 500 to 1000 msec) necessary for the execution of the pulse sequence of each time passes (step S10). Then, whether the count of the numbering counter CNT reaches the preset upper limit or not is determined (step S11). In cases where, for example, five two-dimensional images are produced with the delay time $T_{DL}$ changed into various amounts for the purpose of optimizing the synchronization timing, the count in the counter CNT is set to "5." If the count has not yet reached the upper limit (No at step S11), the processing is returned to step S5 to repeat the above processing. In contrast, the count of the counter CNT equals the upper limit (Yes at step S11), a command to release the breath hold is sent to the voice generator 16 (step S12), and the processing returns to the main program. A voice message to release the patient from the breath hold is such that "you may breathe."

Executing the above processes sequentially leads to the execution of the preparing pulse sequence of which timing is exemplified in FIG. 4. For example, when the initial time $T_0=300$ msec and the time interval $\Delta T=100$ msec are set, the delay time $T_{DL}$ to determine the synchronization timing is adjusted to 300 msec for the first scanning, 400 msec for the second scanning, 500 msec for the third scanning, and so on.

Therefore, when the first R-wave peak appears after the instructions of the breath hold, the first scan $IMG_{prep1}$ based on, for example, a two-dimensional FASE method is executed so that it lasts for a certain period of time (for example, approx. 500 to 1000 msec) from a certain time instant when the delay time $T_{DL}(=T_0)$ has elapsed after the R-wave peak appearance, whereby echo signals being acquired. Whenever the next R-wave may appear during the continuation of this sequence, the foregoing waiting process at step S10 in FIG. 3 makes the sequence continue regardless of the R-wave that appeared in the course of execution. Namely, once the sequence starts in synchronization with a certain heartbeat, the execution can continue over the succeeding one or more heartbeats to acquire necessary echo signals.

Unless the count of the numbering counter CNT has yet reached its limit, steps S5 to S11 will be executed again. Thus, in the embodiment as shown in FIG. 4, when the peak of the third R-wave is accomplished and then the delay time $T_{DL}=T_0+T_{inc}=400$ msec passes, the second scan $IMG_{prep2}$ is launched and continued for the given period, echo signals being acquired as well. When the next R-wave appears after the second sequence and then the delay time $T_{DL}=T_0+2 \times T_{inc}=500$ msec passes, the third scan $IMG_{prep3}$ starts and continues for the given period, echo signals being also acquired. Like the above, when the next R-wave appears after the third sequence and then the delay time $T_{DL}=T_0+3 \times T_{inc}=600$ msec passes, the fourth scan $IMG_{prep3}$ starts and continues for the given period to acquire echo signals as well. Such scan is repeated by the number of desired times, for example, a total of five times, to acquire five frames of echo data from the same cross section.

The echo data are sent to the calculation unit 10 via the receiver 8R and then the sequencer 5 in turn. The calculation unit 10 reconstructs image data mapped in the k-space (frequency space) into image data in the real space by means of a two-dimensional Fourier transform. The reconstructed image data are stored in the storage unit 11 as blood flow image data. The host computer 6 responds to, for example, operation signals from the input device 13 so that images of blood flow are sequentially displayed in a dynamic (CINE) mode.

As pictorially shown in FIG. 5, for example, two-dimensional abdominal coronal images of which imaged time phases are mutually different are displayed. In these coronal images, an artery AR and a vein VE are located so that they almost flow in the superior-inferior direction of a body. However, the imaged timing, that is, "the delay time $T_{DL}$=initial time $T_0+T_{inc} \times \Delta T$" from the R-wave is different image by image. An operator observes these images to select one image in which an artery AR and a vein VE are both depicted in the highest intensities and another image in which a vein is depicted alone in the highest intensity. A synchronization timing $T_{DL}$ for a systole is determined to $T_{DL}=T_{DL1}$ using a delay time $T_{DL1}$ that is assigned to the image in which the vein VE is depicted alone in the relatively highest intensity. Similarly, a synchronization timing $T_{DL}$ for a diastole is determined to $T_{DL}=T_{DL2}$ using a delay time $T_{DL2}$ that is assigned to the image in which the artery AR and vein VE are both depicted in the relatively highest intensities.

As described above, from a plurality of blood flow images scanned as the delay time $T_{DL}$ was changed dynamically, the operator decides delay times $T_{DL}$ (for example, two delay times $T_{DL1}$ and $T_{DL2}$) serving as optimum synchronization timings for the systole and diastole by visual observation. And the operator carries out a command, for example, by hand, for reflecting the decided delay times $T_{DL}$ into an imaging scan which will follow.

As to reflecting the decided delay times into the imaging scan, a further configuration can also be realized by using software. The configuration is that when images that have been determined through visual observation are specified, delay times $T_{DL}$ assigned to the specified images are automatically memorized as optimum synchronization timings, and the timings are automatically read out in performing the imaging scan. This makes it possible to specify ECG-synchronized timings in an automatic fashion.

By the way, in the foregoing ECG-prep scan, the phase-encode direction is positively made to agree with the running direction (i.e., body-axis direction) of a blood flow such as the aorta. Compared to cases where the phase-encode direction is set to other directions, this setting of the phase-encode direction leads to clear images in which information about blood flow directions (directional performance) is avoided from being dropped, providing its superior depiction capability.

(1.3) Imaging Scan

Referring to FIGS. 6 to 14, an operation of an imaging scan based on the ECG-synchronized technique of the present embodiment will now be described.

The host computer 6 executes the processes shown in FIGS. 6 and 7 in response to operational information from the input device 13, as part of the execution of a not-shown given main program.

Specifically, first, the host computer 6 reads from, for example, the input device 13 the two optimum delay times $T_{DL}$ determined by the operator through the foregoing ECG-prep scan (step S20). The delay times $T_{DL}$ are an optimum delay time $T_{DL1}$ given to a systole and an optimum delay time $T_{DL2}(>T_{DL1})$ given to a diastole. Information in relation to the optimum delay times $T_{DL1}$ and $T_{DL2}$ may be stored in advance in the storage unit 11.

Then, the host computer 6 inputs information about scan conditions, image processing techniques, and others, which are specified by the operator using the input device 13, processes the information including the delay times $T_{DL1}$ and $T_{DL2}$ into control data, and outputs the control data to both sequencer 5 and operation unit 10 according to their necessity (step S21). The scan conditions include a phase-encode direction, an image size, the number of scans, a waiting time between scans, and a pulse sequence depending on a region to be scanned. The image processing techniques include a subtraction method and its weighting factors, an addition method (simple, averaging, or weighted addition method), and/or a maximum intensity projection (MIP) method.

When it is determined that an instruction indicating the completion of scan preparations has been issued (step S22), a command indicating the start of a breath hold is output to the voice generator 14 (step S23). This causes the voice generator 14 to utter a voice message saying, "Hold your breath, please." like the ECG-prep scan. In response to this message, a patient is to hold breathing (refer to FIG. 8).

After this, the host computer 6 instructs the sequencer 5 to start the imaging scan (step S24).

When having received instructions to start the imaging scan (step S24-1 in FIG. 7), the sequencer 5 begins reading the ECG signal (step S24-2) to determine the appearance of the specified n-th R-wave (reference wave) peak of the ECG signal by using an ECG trigger signal made synchronous with the peak (step S24-3). The reason why the appearance of the R-wave is waited n-times (for example, two times) is to find a timing at which the patient has already in breath hold.

When the specified n-th R-wave has appeared, processing to wait for the delay time $T_{DL1}$ determined for a specified time phase in the systole is executed first (step S24-4). The delay time $T_{DL1}$ is, as explained before, optimized through the ECG-prep scan such that echo signal intensities become the highest in imaging objective venous flows in a systole, providing a superior depiction capability of the entity.

Figure 8:
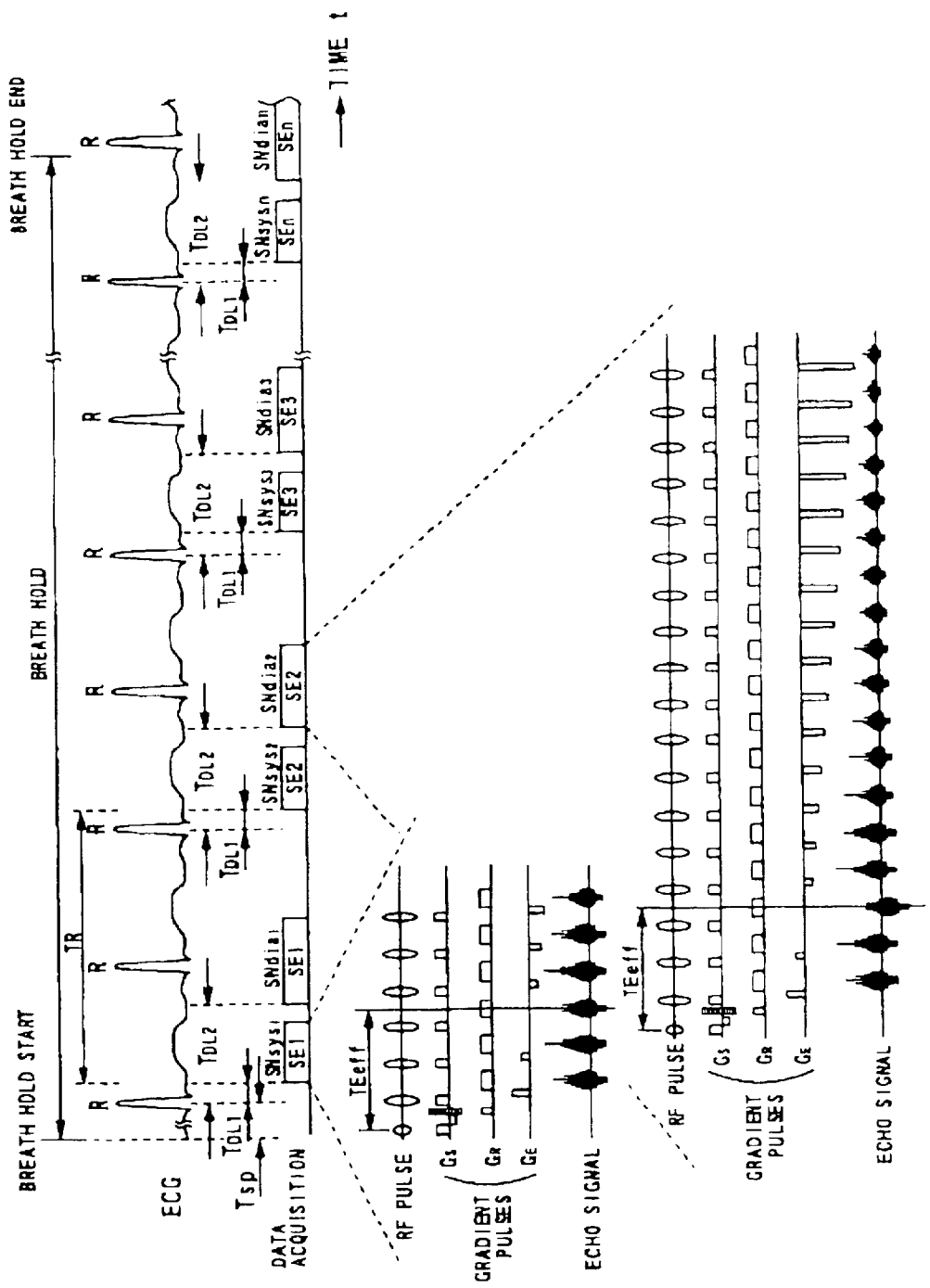
FIG. 8 is a timing chart showing timing of the imaging scan based on an electrocardiogram-synchronized technique in the first embodiment.
Figure 10:
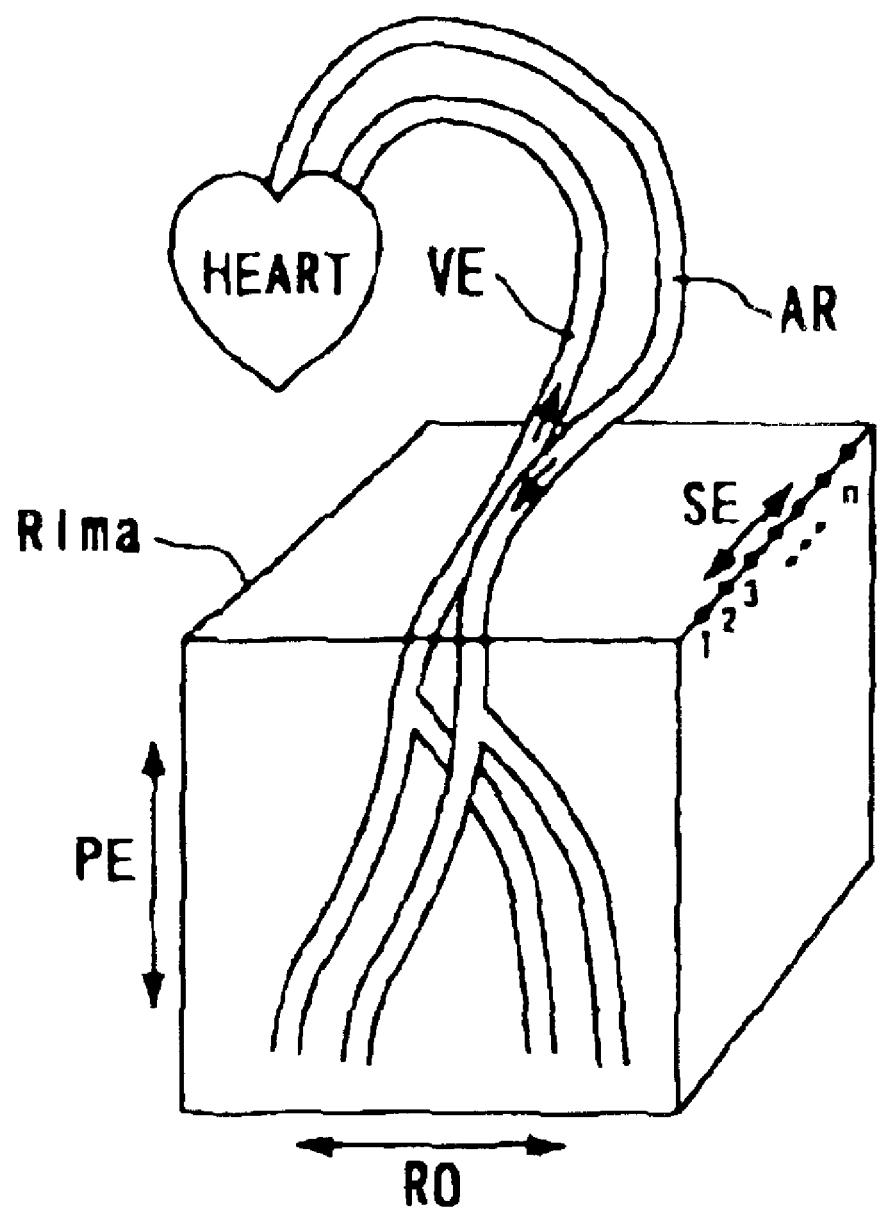
FIG. 10 explains a positional relationship between a three-dimensional volume to be scanned and blood vessels to be imaged.

The sequencer 5 begins to perform the imaging scan for a systole at a time when this optimum delay time $T_{DL1}$ has passed, the time being regarded as an optimum ECG-synchronized timing (step S24-5). Practically, the transmitter 8T and the gradient power supply 4 are driven based on the pulse sequence information memorized beforehand. Thus a scan (the first scan) $SN_{sys1}$ is performed based on the first slice-encode amount SE1 defined by, for example, a three-dimensional FASE pulse sequence according to the ECG-synchronized technique, as shown in FIG. 8. In this scan, it is preferred that the phase-encode direction PE is made to nearly agree with a specified direction, that is, the flowing direction of blood (artery AR and vein VE), as shown in FIG. 10, for example. Additionally it is preferred that the echo train spacing in the pulse sequence is shortened to 5 msec or thereabouts.

Figure 9:
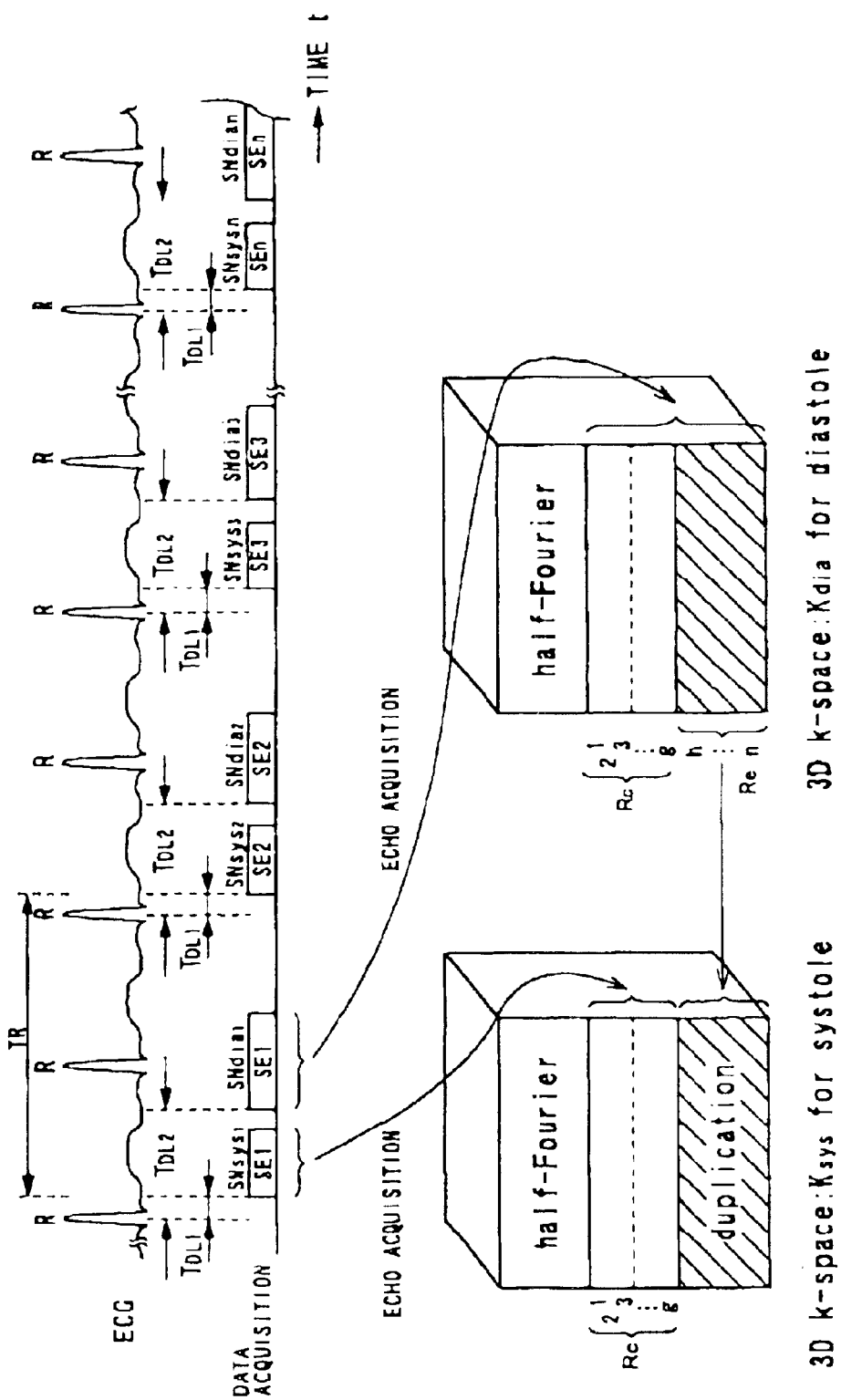
FIG. 9 is an illustration pictorially showing data acquisition at two time phases in performing the imaging scan and k-spaces into which acquired data are mapped.

In the pulse sequence used for the scan $SN_{sysn}$ in the systole, the number of echoes is decreased as seen in FIG. 8, so that generation of echoes is completed in a small period of time remaining one heartbeat. The number of echoes is determined to be able to acquire echo data to be mapped in only a central region (lower-frequency region) Rc in the phase-encode direction ke of the k-space for each slice-encode amount, as pictorially shown in FIG. 9. The next scan (the second scan) $SN_{dian}$ for the diastole can therefore be launched, as shown in FIGS. 8 and 9, in the same heartbeat as the scan $SN_{sysn}$ for the systole. Echo data that are short in a k-space for the systole (the first k-space) $K_{sys}$ are obtained by both of data duplication from a later-described k-space for the diastole (the second k-space) $K_{dia}$ and calculation based on the half-Fourier method (refer to FIG. 9).

Thus, under the first slice-encode amount SE1, echo signals are acquired during a short scan time of about several hundreds msec from a three-dimensional imaging region $R_{ima}$ set to, for example, the hypogastrium as shown in the FIG. 10.

The sequencer 5 then proceeds to scan control for the diastole. Specifically, processing to wait for the delay time $T_{DL2}$ that is determined for a specific time phase in the diastole is performed (step S24-6). As described before, the ECG-prep scan permits the delay time $T_{DL2}$ to be optimized to an amount that produces echo signals into the highest intensity in imaging targeted arterial and venous flows in a diastole, providing a superior depiction capability of the entities.

The sequencer 5 begins to perform the imaging scan for the diastole at a time when this optimum delay time $T_{DL2}$ has passed, the time being regarded as an optimum ECG-synchronized timing (step S24-7). Practically, the transmitter 8T and the gradient power supply 4 are driven based on the pulse sequence information memorized beforehand. Thus a scan $SN_{sys2}$ is performed based on the first slice-encode amount SE1 defined by, for example, a three-dimensional FASE pulse sequence according to the ECG-synchronized technique, as shown in FIG. 8. Echo train spacing in this pulse sequence is set to approximately 5 msec.

The pulse sequence used for the scan $SN_{dian}$ for the diastole is determined, as shown in FIG. 8, to produce more echoes than those for the systole, but produce fewer echoes in number than those fulfilling up the entire k-space by the number of echoes reduced by using the half-Fourier method. As illustrated in FIG. 9, the number of echoes is determined to acquire, every slice-encode amount, echo data that are mapped in a limited region consisting of a central region (lower-frequency region) Rc and one region Re of its outside end regions (higher-frequency regions) in the phase-encode direction ke of the k-space. As will be described later, echo data that will be short in a k-space $K_{dia}$ for the diastole are computed according to the half-Fourier method. The scan $SN_{dia1}$ in this diastole is normally performed over the next heartbeat, as shown in FIGS. 8 and 9.

Thus, under the first slice-encode amount SE1, echo signals are acquired during a scan time of about 600 msec from the three-dimensional imaging region $R_{ima}$ set to the hypogastrium as shown in the FIG. 10.

On having completed the first imaging scan, the sequencer 5 determines if the final imaging scan has been completed or not (step S24-8). In the case of NO at this determination (the final scan has not been completed yet), with monitoring the ECG signal, waiting is done until a shortly set period of time (for example, 2 heartbeats (2R-R) from the R-wave used in the imaging scan) passes. This results in that the recovery of longitudinal magnetization of spins in the stationary parenchyma is actively suppressed (step S24-9).

After waiting for a period of time corresponding to, for example, 2R-R, when the third R-wave appears (YES at step S2497), the sequencer 5 returns its processing to the foregoing step S24-4.

Hence, at a time instant when the specified delay time $T_{DL1}$ has passed since the third R-wave peak, a second scan $SN_{sys2}$ for the systole is commenced in the same way as the above under the next slice-encode amount SE2. Echo signals are therefore acquired from the three-dimensional imaging region $R_{ima}$ (steps S24-4 and S24-5). Then, at a time instant when the specified delay time $T_{DL2}$ has passed since the third R-wave peak, a second scan $SNd_{dia2}$ for the diastole is commenced in the same way as the above under the next slice-encode amount SE2. Echo signals are therefore acquired from the three-dimensional imaging region $R_{ima}$ (steps S24-6, 7).

Likewise, echo signals are acquired for each of the systole and diastole until the final slice-encode amount SEn (for example n=8).

On having completed the final scan $SN_{sysn}$ and $SN_{dian}$ under the slice-encode amount SEn, the determination at step S24-8 becomes YES, thus a notification stating the completion of the imaging scan is sent from the sequencer 5 to the host computer 6 (step S24-10). Accordingly the processing is returned to the host computer 6.

When receiving the notification stating the completion of the imaging scan from the sequencer 5 (FIG. 6, step S25), the host computer outputs a command to release the breath hold to the voice generator 16 (step S26). The voice generator 16 responsively utters a voice message saying, for example, "You may breathe." toward the patient to terminate the period of breath hold (Refer to FIG. 8).

Therefore, as pictorially shown in FIG. 8, the ECG-synchronized scan is performed n-times (e.g., n=8) for each of the systole and diastole every 2R-R on the basis of the 3D-FASE method, for example.

Echo signals emanated from the patient P are received scan by scan by the RF coil 7, then sent to the receiver 8R. The receiver 8R processes the echo signals with various kinds of preprocessing to convert them into digital quantities. The digital echo data are sent via to the sequencer 5 to the calculation unit 10, where they are mapped in each of two three-dimensional k-spaces $K_{sys}$ and $K_{dia}$ formed by memories, correspondingly to the phase-encode amounts and slice-encode amounts.

(1.4) Data Processing and Image Display

Figure 11:
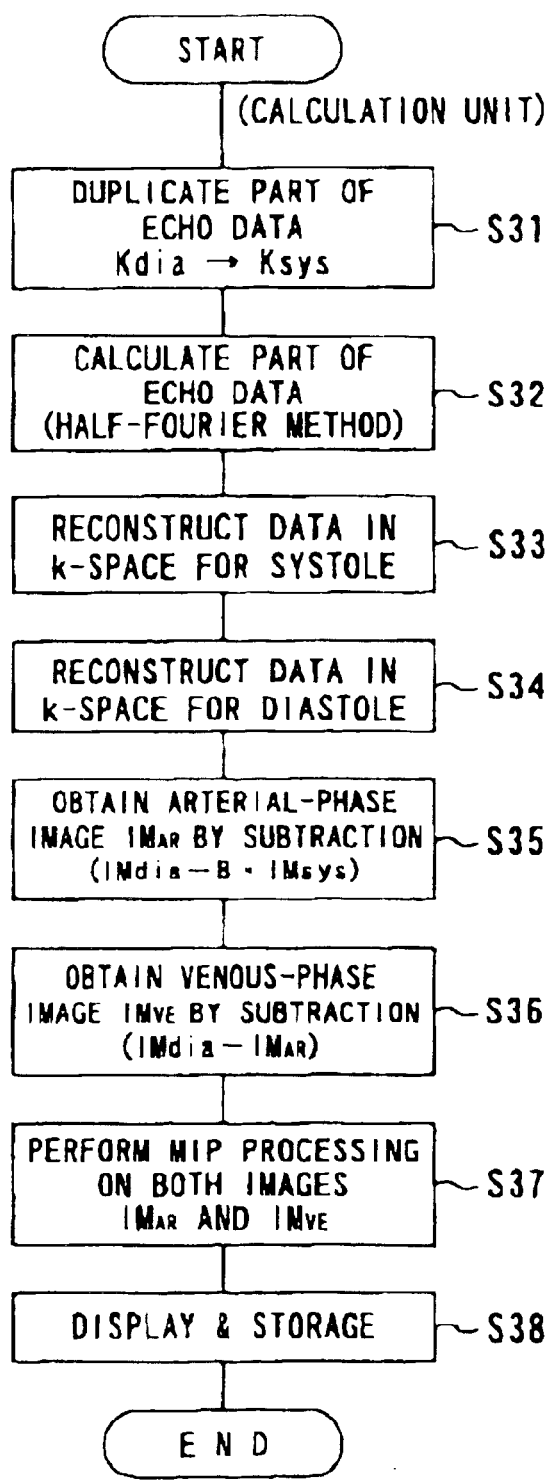
FIG. 11 is an outlined flowchart explaining calculation processing of echo data, which is performed by a calculation unit in the first embodiment.
Figure 12:
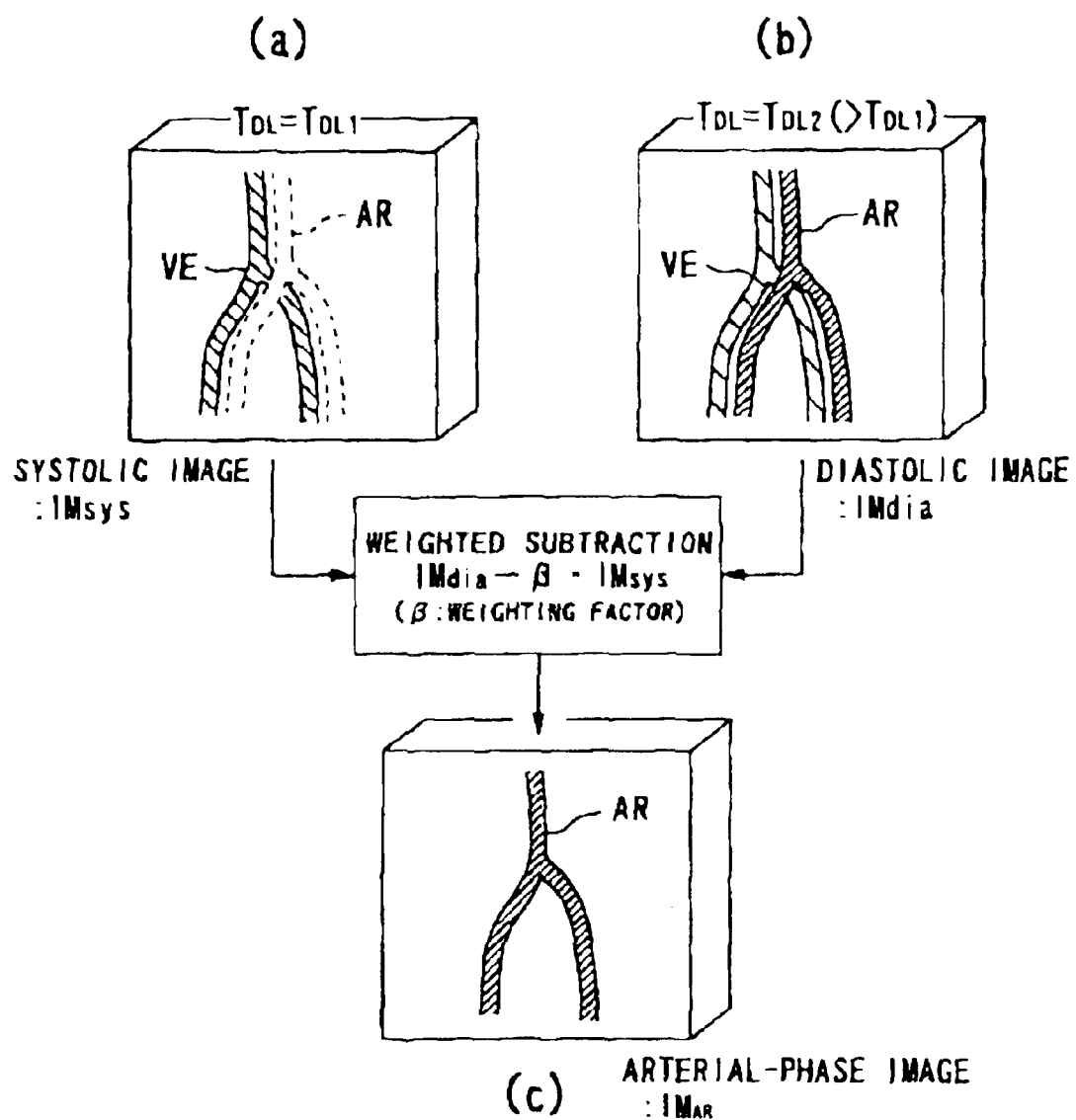
FIG. 12 is a pictorial illustration explaining the outline of subtraction for producing an arterial phase image.
Figure 13:
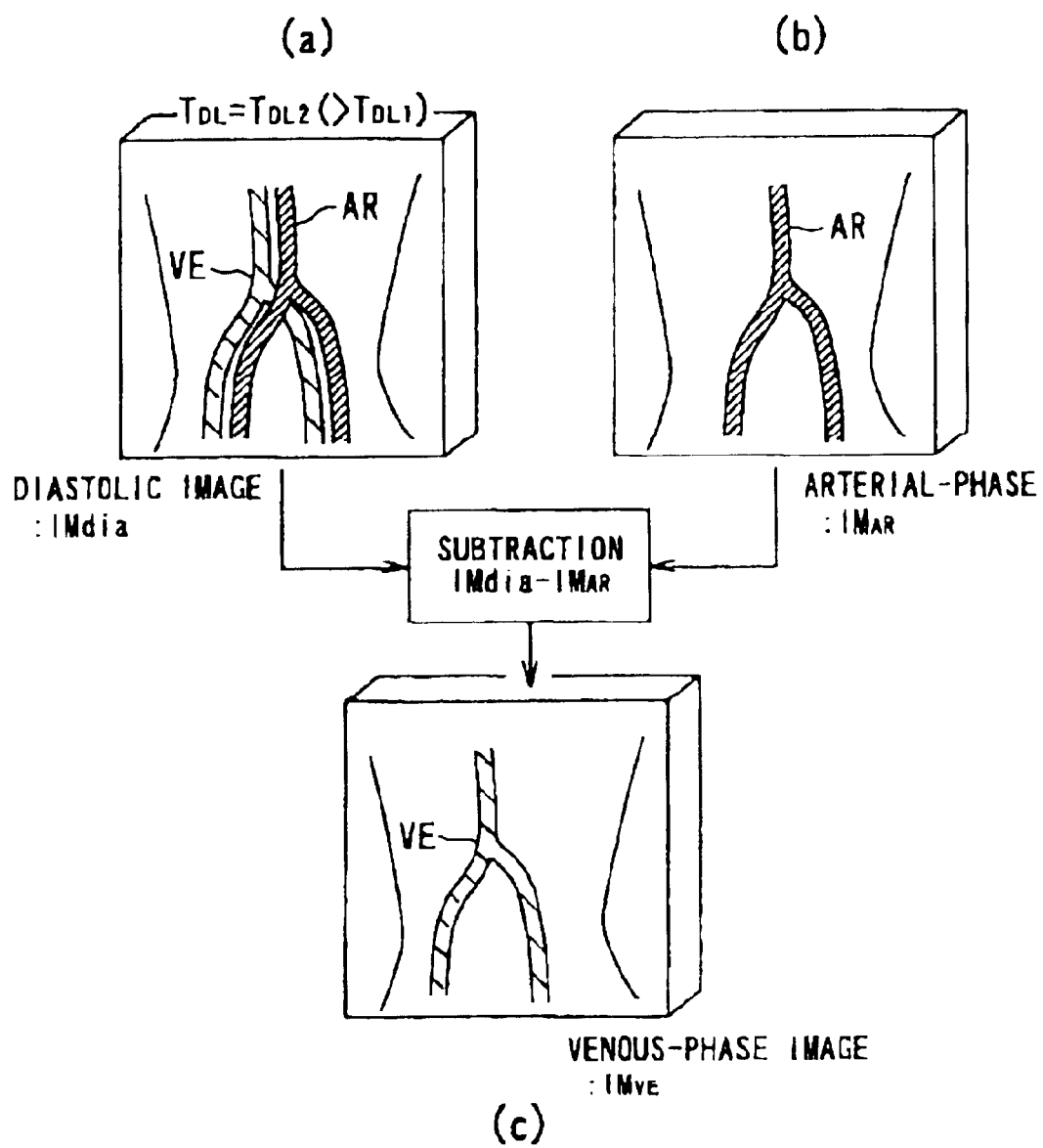
FIG. 13 is a pictorial illustration explaining the outline of subtraction for producing a venous phase image.

After the echo data acquisition, the host computer 6 instructs the calculation unit 10 to execute the processing shown in FIG. 11.

As shown in FIG. 11, in response to the instructions from the host computer 6, the calculation unit 10 will complete mapping of all data in both systole-use k-space $K_{sys}$ and diastole-use k-space $K_{dia}$ (steps S31 and S32). Specifically, at step S31, as illustrated in FIG. 9, echo data belonging to one of two high-frequency regions in the phase-encode direction of the diastole-use k-space $K_{dia}$ (in FIG. 9, echo data belonging to the phase encoding numbers h to n) are duplicated to their corresponding positions in the systole-use k-space $K_{sys}$. Those duplicated echo data correspond to data that had not been acquired in the time of the scans for the systole. Then at step S32, both systole-use k-space $K_{sys}$ and diastole-use k-space $K_{dia}$ undergo the half-Fourier technique on the basis of the complex-conjugate relationship, respectively, thereby computing echo data that will be mapped in a remaining region of each k-space in which echo data had not been acquired so far. Through the processing at steps S31 and S32, both k-spaces $K_{sys}$ and $K_{dia}$ are entirely filled with data.

The calculations unit 10 then reconstructs images by performing a three-dimensional Fourier transform in relation to the k-space $K_{sys}$ for systole and k-space $K_{dia}$ for diastole, respectively (steps S33 and S34). Accordingly, as shown in FIGS. 12(a) and (b), there are provided three-dimensional data of both of an image (systolic image) $IM_{sys}$ at the delay time $T_{DL1}$ falling into the systole and an image (diastolic image) $IM_{dia}$ at the delay time $T_{DL2}$ falling into the diastole. The systolic image $IM_{sys}$ contains, in general, only image data of a vein, and it hardly contain those of an artery. By contast, the diastolic image $IM_{dia}$ contains both of image data of the artery and vein, though depicted states of the artery and vein may be different from each other.

Hence, in order to obtain an arterial-phase image $I_{AR}$, the calculation unit 10 performs the subtraction of "$IM_{dia}$–$IM_{sys}$" pixel by pixel (step S35). Here, β is a weighting factor. By designating an appropriate amount to the weighting factor β, this subtraction allows image data of the vein VE to be nearly diminished to zero, thus providing three-dimensional image data of an arterial-phase image $IM_{AR}$ containing only the artery AR, as pictorially shown in FIG. 12.

Further, to obtain a venous-phase image $IM_{VE}$, subtraction of "$IM_{dia}$–$IM_{AR}$" is performed on the pixel basis (step S36). The image data $IM_{AR}$ used in this calculation have been derived by the weighted-subtraction described above. This causes image data of the artery AR to reduce to zero, thereby providing three-dimensional image data of a venous-phase image $IM_{VE}$ containing only the vein VE. This subtraction can also be replaced by weighted-subtraction.

Figure 14:
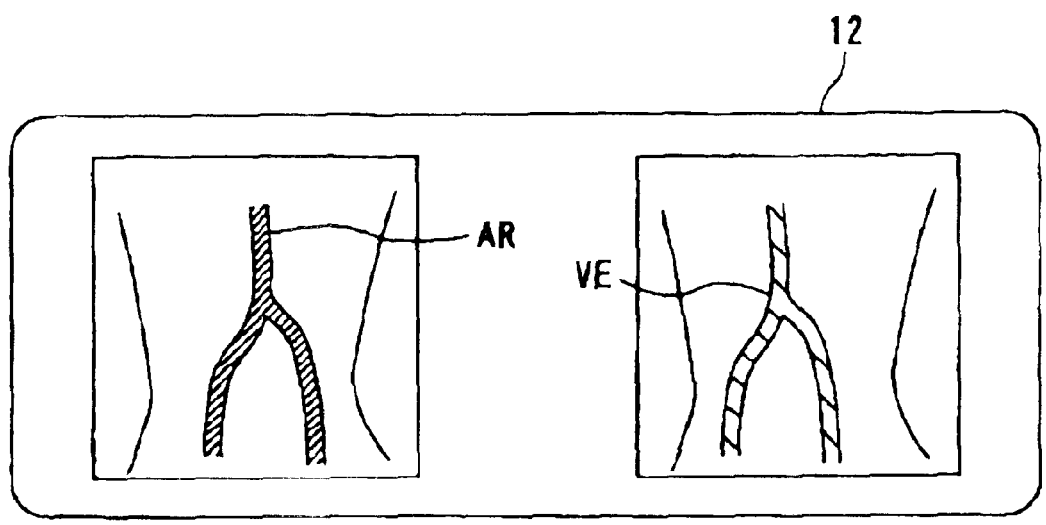
FIG. 14 exemplifies simultaneous display of both arterial and venous phase Images.

After such subtraction, the calculation unit 10 performs MIP (maximum intensity projection) processing with each of the arterial-phase image $IM_{AR}$ and venous-phase image $IM_{VE}$. This produces data of a two-dimensional image (for example, coronal image) viewed along a desired observing direction of blood vessels (step S37). These two-dimensional images of the arterial- and venous-phases are displayed on the display unit 12 as shown in FIG. 14 and stored into the storage unit 11 (step S38).

(1.5) Operations and Advantages

As descried above, in the MRI system of the present embodiment, appropriate scan start timings (i.e., delay times from the R-wave) are determined for each of the systole and diastole. Then, at the timings, the scans of two shots for the systole and diastole are individually and sequentially performed under each slice-encode amount. In addition, the systolic-use scan that always precedes in each cardiac cycle is shorter in data acquisition time (the number of echoes) so that it does not overhang the following diastolic-use scan in time. Echo data acquired by the systolic-use scan are mapped in a lower-frequency region of the systolic-use k-space that is most significant in improving contrast. The remaining data in the systolic-use k-space, which have not been acquired, are duplicated from part of data acquired by the following diastolic-use san that is allowed to acquire echoes during a longer period of time. Moreover, the scans for the systole and diastole adopt the half-Fourier technique in order to set the scan time as short as possible.

Accordingly, the two-shots of scans for the systole and diastole, which are performed under one slice-encode amount, usually remain within an interval of two heartbeats. Consecutively repeating such scans enables a three-dimensional scan such that echo data of each of systolic and diastolic blood flows are acquired at appropriate timings during one time of breath hold duration in three-dimensional scanning. In other words, three-dimensional image data of blood flows in each of the systole and diastole are obtained by one time of imaging performed at proper timings. The acquired data are then subjected to the reconstruction and subtraction described before, thereby arterial-phase and venous-phase images being provided.

In the present embodiment, it is therefore unnecessary to perform imaging scans (i.e., in total, two times of scans) for the systole and diastole in a separated fashion, and one time of scan is enough. Therefore, the scan time is reduced largely and throughput of patients is improved. Particularly, an effect of shortening the san time becomes noticeable in three-dimensional scanning. Furthermore, misregistration due to patient's body motions can be lessened markedly, thereby images of higher quality being provided. Further, using echo data acquired at two cardiac phases through one time of imaging, blood flow images (MRA images) in which arterial and venous phases are visually separated can be obtained. Thus, the imaging can be done with improved efficiency, while blood flow information supplied can be enriched.

Because most optimum ECG-synchronized timings for the systole and diastole are determined in advance through the ECG-prep scan, it is possible that target blood flows are traced in a steady manner at each phase during the systole and diastole. This provides blood flow images of which signal intensity is higher, blood flow contrast is improved, and S/N is superior. On the other hand, previously setting appropriate ECG-synchronized timings eliminates the need of re-performing scans in most cases, thus relieving operational burdens on operators and physical and mental loads on patients.

Further, in addition to shortening the repetition time TR and echo train spacing, the phase-encode direction can be made to approximately agree with a blood-flow direction and the slice direction can be set along the front/rear direction of a patient. Compared to the TOF technique that requires slices to be set perpendicular to a blood flow, the entire scan time can therefore be shortened. Further, since the number of applications of the slice encode is reduced by an amount corresponding to a shortened scan range in the slice direction, the whole scan time is reduced largely, compared to the conventional TOF or phase encode technique. This will lead to a reduced burden on patients and an improved throughput of patients.

Additionally, because it is unnecessary to inject a contrast medium into an object, non-invasive imaging can be provided. This will also result in largely lessened mental and physical burdens on a patient. Cumbersome operations inherent to the contrast technique, such as paying attention to a contrast effect of the contrast medium, are not required as well. Thanks to those advantages, differently from the contrast technique, the imaging can be performed repeatedly if necessary.

Further, because the phase-encode direction is made to agree or nearly agree with a running direction of vessels, blurs of pixels can be utilized positively. This provides a remarkable depiction capability in the running direction of vessels. Further, by changing the phase-encode direction according to the vessel-running direction in a portion to be imaged, various portions of an object can be imaged with ease.

Because the present embodiment uses the pulse sequence based on the fast SE technique, the imaging is advantageous in susceptibility and contour distortion, (1.6) Modifications of First Embodiment The present invention is not limited to the configuration described in the above embodiment, but it can be modified into various ways and practiced into various applications.

For example, in the foregoing embodiment, the configuration has been made such that both arterial-phase and venous-phase images are present. In this respect, only an arterial-phase image can be produced by the subtraction and displayed. By this modification, the subtraction step S36 in FIG. 11, which is directed to production of a venous-phase image, can be omitted. In contrast, with the subtraction for arterial-phase and venous-phase images still left, it can be configured so that the arterial-phase image is displayed alone.

In the foregoing embodiment, each of the scans for the systole and diastole has been conducted by scanning based on the half-Fourier technique, but the scanning will not always be confined to a technique based on the half-Fourier technique. In such a case, the scan for the diastole is performed to acquire data mapped entirely into the k-space, and echo data mapped in its high-frequency regions positioned at both end sides in the slice-encode direction are duplicated to corresponding regions in the k-space for the systole.

The three-dimensional scanning has been employed by the foregoing embodiment, but the two-dimensional scanning can be used as well. Pulse sequences that are possible to be employed are not limited to the FASE method, but other pulse sequences derived from the FSE or EPI method may be used as well.

Moreover, the post-processing of echo data in the foregoing embodiment has been configured such that the echo data are once converted to image data in the real space, then the subtraction is performed to obtain the arterial-phase and venous-phase images. Alternatively, the subtraction may be done such that it is performed at the stage of echo data on the k-spaces $K_{sys}$ and $K_{dia}$ of which matrix sizes are the same to each other. Echo data resulted from the subtraction then undergo a reconstruction process to provide blood flow images.

The technique to obtain arterial-phase and/or venous-phase images is not limited to the subtraction between data acquired at the two different cardiac phases described in the embodiment. Alternatively, there may be provided a technique of performing subtraction between images of which echo train spacing are different from each other, or a technique of performing subtraction between images of which effective TE times are different from each other. Differences in the echo train spacing give changes to sensitivity in detecting speed of blood flows. This allows acquisition of echo data into which differences in blood flow speed due to inherence of the artery and vein are reflected. Therefore, the subtraction that will be performed in the similar way to the above can provide blood flow images of the artery and vein. In addition, differences in the effective TE time enables echo data to be acquired as the artery and vein of which T2 time differs from each other are differentiated. Thus the similar subtraction to the above can provide blood flow images of the artery and vein.

(2) Second Embodiment

Referring to the foregoing drawings and FIGS. 15 to 22, a second embodiment of the present invention will now be described.

MR imaging according to the second embodiment is characterized in that a dephasing or rephasing pulse is added to the read-out gradient pulse $G_R$ in order to depict slow-speed blood flow such as blood flow in the inferior limb. The present embodiment uses an MRI system that is the same or identical in both hardware configuration and ECG-prep scan as or to those in the first embodiment.

(2.1) Imaging Scan

Figure 15:
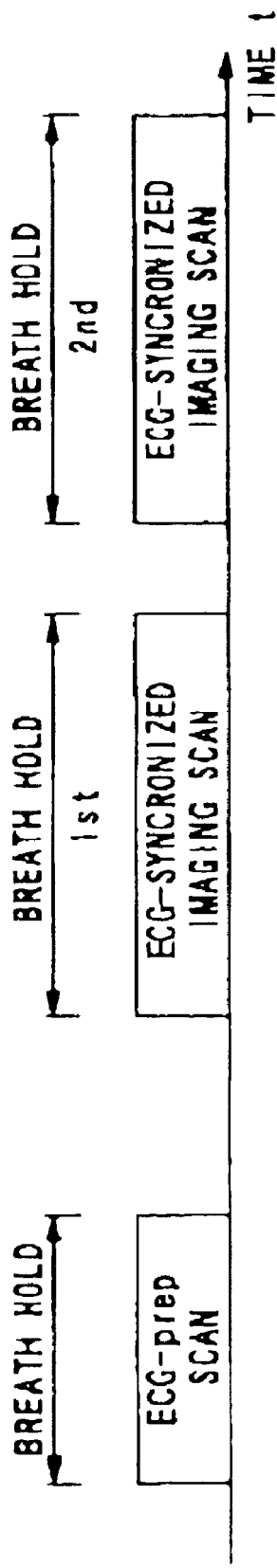
FIG. 15 explains a time-sequential relationship between an ECG-prep scan and two times of an imaging scan in a second embodiment.
Figure 16:
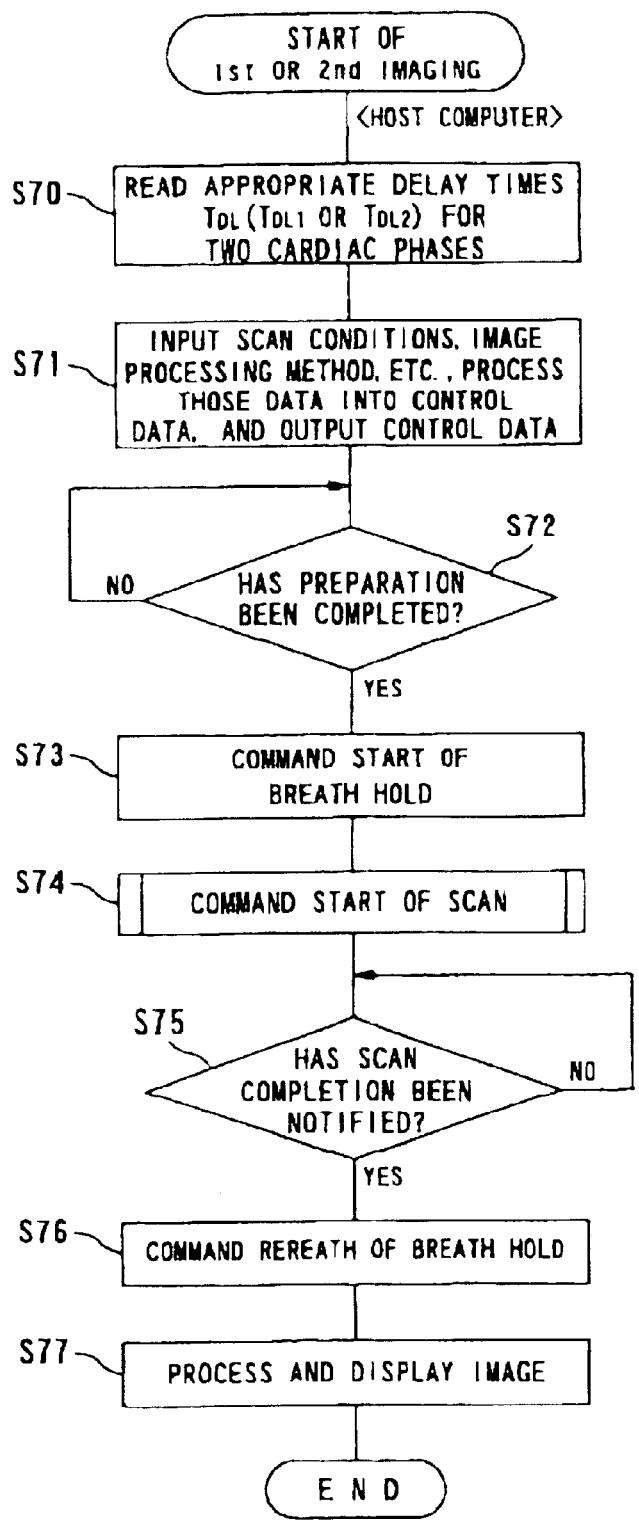
FIG. 16 is an outlined flowchart exemplifying imaging scans performed first and second in the second embodiment.

In the present embodiment, as shown in FIG. 15, the ECG-prep scan is followed by two times of imaging scans each performed on the ECG-synchronized technique by which the two synchronization timings are used, respectively.

Referring to FIGS. 16 to 20, operations of the imaging scans of two times (namely, imaging of two times) will now be described. The host computer 6 executes a not-shown given main program, during which time it executes processing of each imaging scan shown in FIG. 16 in response to an operation information from the input device 13.

Now suppose that the first time of imaging scan (imaging) is assigned to the systole. In this case, the host computer 6 first read, for example, from the input device 13, an optimum delay time $T_{DL}$ ($=T_{DL1}$ or $T_{DL2} > T_{DL1}$) dedicated to the systole, which is determined by an operator through the foregoing ECG-prep scan (step S70).

The host computer 6 then inputs scan conditions and information about image processing that the operator specified from the input device 13, before processes those inputs into control data to be outputted to both of the sequencer 5 and calculation unit 10 (step S71). The scan conditions include an applied direction of the read-out gradient pulse, an image size, the number of times of scanning, an interval between scans, a pulse sequence according to a portion to be scanned, and others. The image processing information includes information indicative of MIP processing and/or subtraction. In the case of subtraction, the information shows that the subtraction is simple subtraction, weighted subtraction, or addition. Further, the control data include the delay time $T_{DL}$.

Like the first embodiment, when it is determined that the preparation for scanning has been notified (step S72), a command of starting a breath hold (step S73), a command of starting the scans (step S74), a determination whether the scans have been completed or not (step S75), a command of releasing the breath hold (step S76), and instructions to image processing and display (step S76) are performed in turn.

At step S74, to be specific, the host computer 6 instructs the sequencer 5 to start the first-(or second-)time imaging scan.

On receiving such instructions to start the imaging scan (step S74-1, FIG. 17), the sequencer 5 begins to read the ECG signal (step SW74-2), and detects the appearance of peak value of a given n-th R-wave (reference waveform) of the ECG signal on the basis of ECG triggering signals synchronized with the peak values (step S74-3). When the n-th R-wave appears, waiting will be done during the specified delay time $T_{DL1}$ (step S74-4).

When the optimum delay time $T_{DL1}$ (or $T_{DL2}$) has passed, it is regarded that an optimum ECG-synchronized timing has come. The sequencer 5 therefore performs the first-time imaging scan (step S74-5). Specifically, the sequencer 5 drives the transmitter 8T and gradient power supply 4 according to information concerning a pulse sequence stored already. As a result, the first-time imaging scan (i.e., imaging) based on a pulse sequence using the three-dimensional FASE technique is executed with the ECG-synchronized technique, as shown in FIGS. 18A and 18C (in FIG. 18C, the phase-encode gradients are omitted from being drawn).

Figure 20:
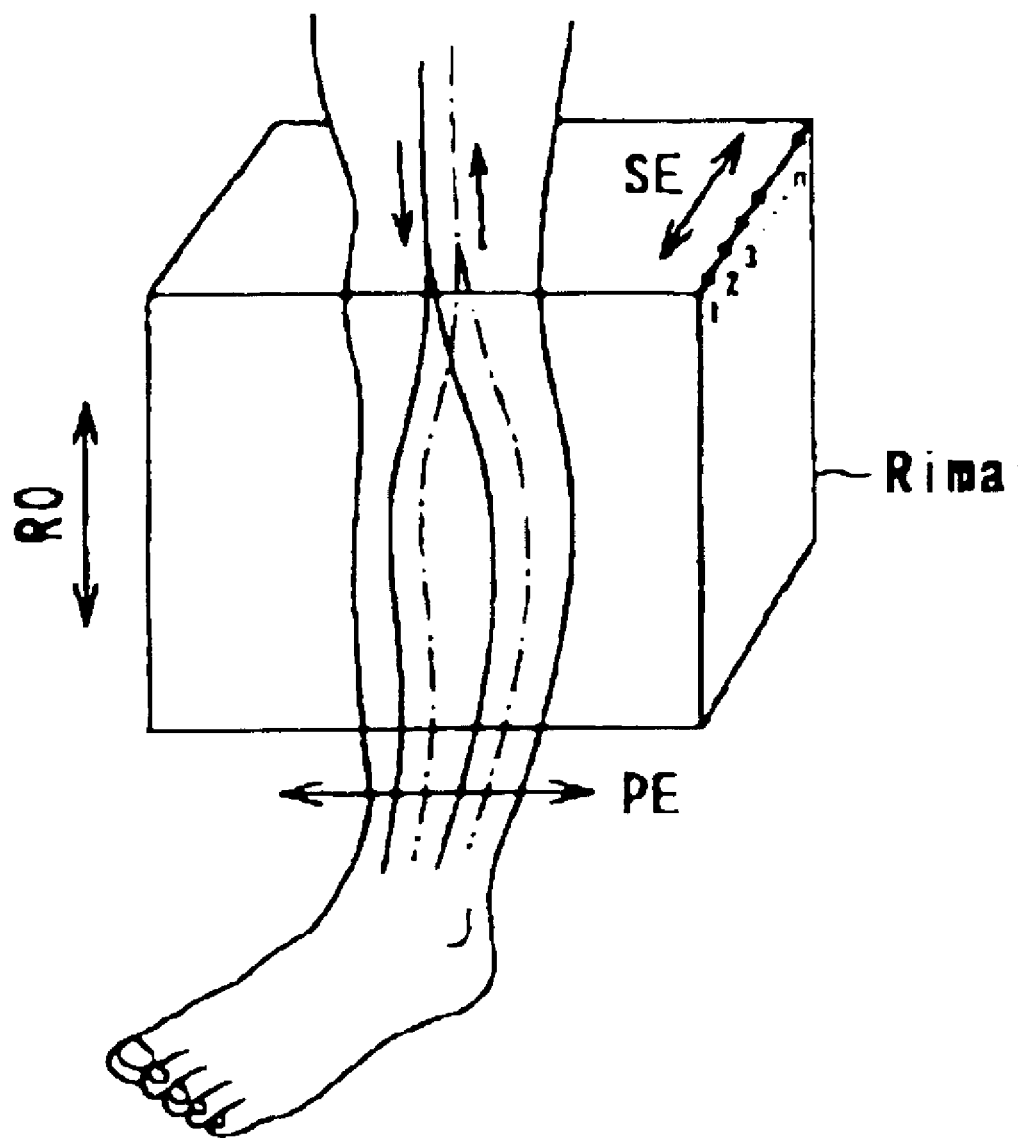

In this imaging on this pulse sequence, the read-out gradient pulse $G_R$ is applied in a direction RO, as shown in FIG. 20, which substantially agrees with directions of blood flows (artery AR and vein VE) in an object to be scanned.

Figure 19A:
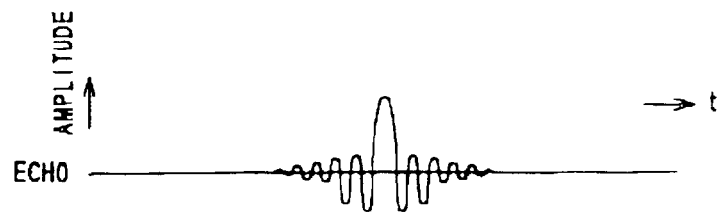
FIGS. 19A to 19C are illustrations showing dephasing pulses and rephasing pulses added to a readout gradient, FIG. 20 explains a positional relationship between a three-dimensional volume to be scanned and blood vessels to be imaged in the second embodiment.
Figure 19B:
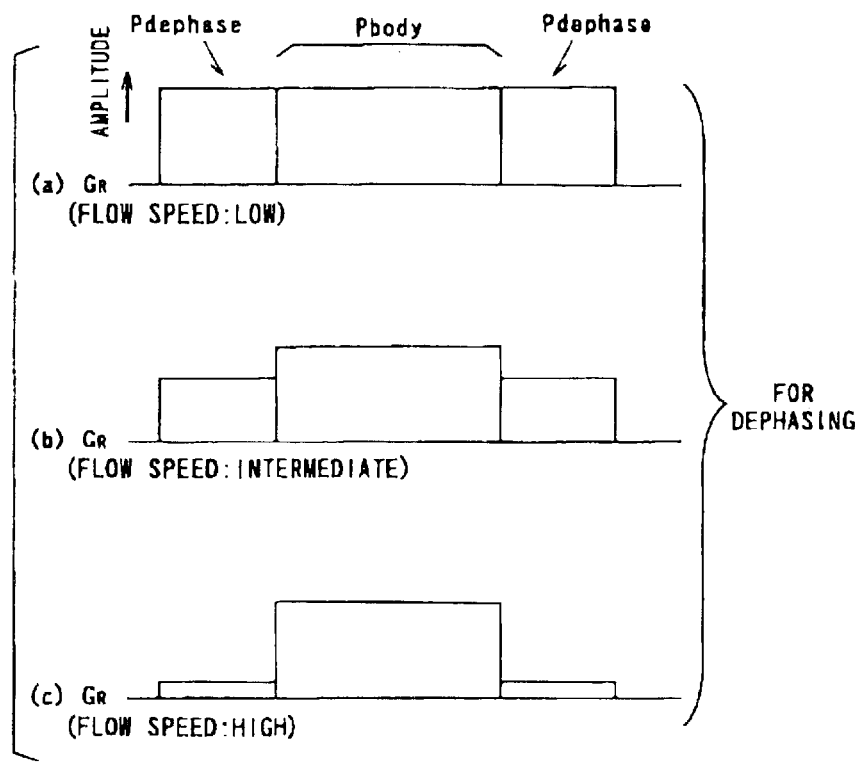

The read-out gradient pulse $G_R$ included in the pulse sequence is provided, as shown in FIGS. 18C, 19A and 19B, with a frequency-encoding pulse body $P_{body}$ for acquiring echo signals and two dephasing pulses $P_{dephase}$, which serve as control pulses, continuously added to the temporal forward and backward ends of the pulse body $P_{body}$. The dephasing pulses $P_{dephase}$ are the same in polarity as the frequency-encoding pulse body $P_{body}$, and promote dephasing of magnetic spins in motion.

In contrast, the dephasing pulses $P_{dephase}$ gives few dephasing effect to stationary or almost stationary magnetic spine. It is therefore significant that the read-out gradient pulse $G_R$ be applied substantially in a direction along which fluid (blood and lymph) to be imaged moves.

Preferably, the dephasing pulses $P_{dephase}$ are changeable or controllable in its intensity in accordance with flow speeds of lymph or blood, which is fluid to be imaged. FIG. 19B shows examples in which the intensity of the dephasing pulses $P_{dephase}$ is decreased in turn. In general, control is made such that the intensity of the dephasing pulses $P_{dephase}$ is reduced as the speed of blood flow becomes higher.

Figure 19C:
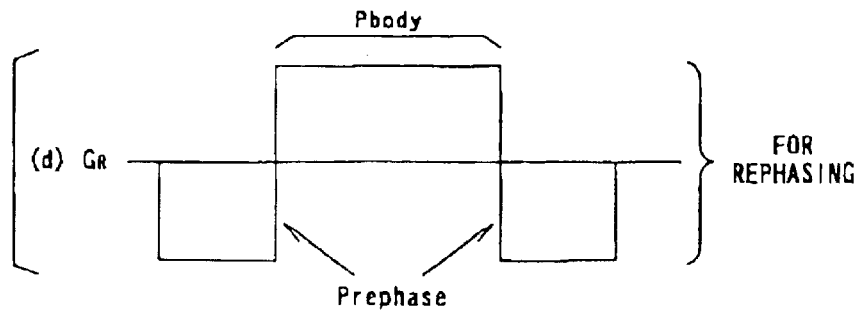

When fluid (such as blood flow) to be imaged is relatively high in speed, a total of two rephasing pulses $P_{rephase}$ are continuously added to the temporal forward and backward ends of the pulse body $P_{body}$, as shown in FIGS. 19A and 19C. The rephasing pulses, which also serve as control pulses, are opposite in polarity to the frequency encoding pulse body $P_{body}$, so that they rephase magnetic spins so as to suppress an excessive amount of dephasing of the spins, thus suppressing artifacts. It is preferable to alter the intensity of the rephasing pulses $P_{rephase}$ according to flow speeds of an object.

In this first embodiment, the first and second (later described) imaging scans employ the read-out gradient pulse $G_R$ to which either dephasing pulse $P_{dephase}$ or rephasing pulse $P_{rephase}$ is added.

Executing the three-dimensional FASE pulse sequence makes it possible that echo signals stimulated by both of the excitation 90-degrees RF pulse and the refocusing 180-degrees RP pulses are acquired at each phase-encode amount assigned to each slice-encode amount. In each echo signal, dephasing of phase of magnetic spins caused by the dephasing pulse $P_{dephase}$ or rephasing of phase of magnetic spins caused by the rephasing pulse $P_{rephase}$ is reflected.

This reflection will also be detailed together with a display operation described later, but the summary thereof is as follows.

To fluid that is flowing along an applied direction of the read-out gradient pulse, a dephasing effect caused by the dephasing pulse $P_{dephase}$ promotes the flow void effect. Thus the dephasing pulse reduces the intensity of an echo signal. In the case that the fluid hardly flow along such direction, only a smaller amount of promotion of the flow void effect is available due to the dephasing pulse $P_{dephase}$, thereby the intensity of an echo signal being not so much reduced.

In the case of the rephasing pulse $P_{rephase}$, its rephasing effect is able to control degrees of dephasing according to flow speeds of fluid.

Echo train spacing in the foregoing pulse sequence is shortened to an amount as small as approximately 5 msec. Under the first slice-encode amount SE1, echo signals are acquired from a three-dimensional imaging region Rima directed to, for example, the inferior limb as shown in FIG. 20 for a scan time of approximately 600 msec.

Figure 17:
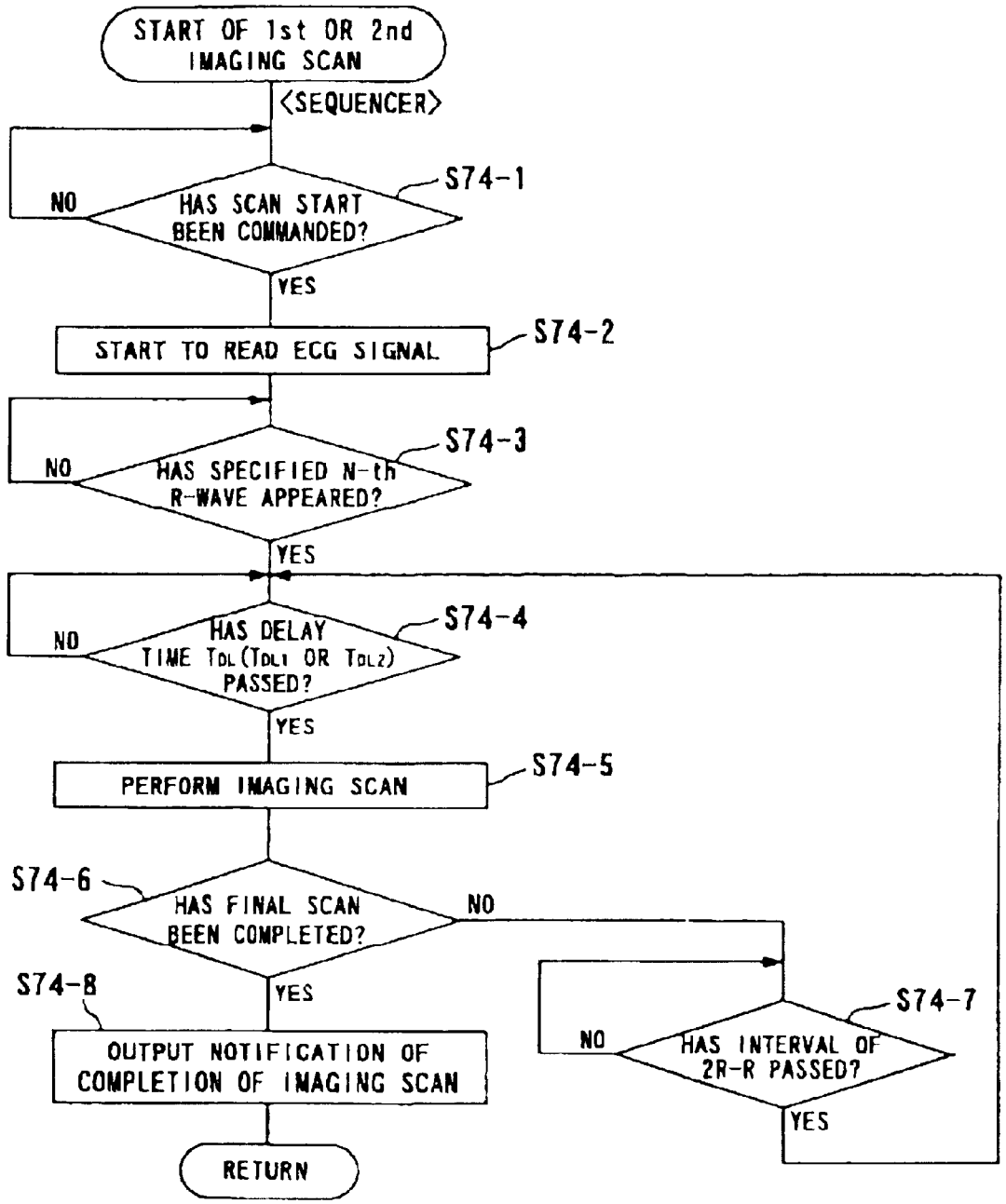
FIG. 17 is an outlined flowchart exemplifying imaging scans performed first and second in the second embodiment.

When the scanning has been completed at the first slice encoding, the sequencer 5 determines whether or not the scanning under the final slice encoding has been completed (step S74-6, in FIG. 17). If this determination is NO (the scanning under the final slice encoding has not been completed yet), the sequencer 5 waits for a period of time, which is set to a rather shorter period, such as two heartbeats (2R-R) starting from the R-wave used for the last imaging scan, as it monitors the ECG signal (step S74-7). A repetition time TR is set to an amount of four heartbeats (4 R-R) or less.

In this way, waiting for a period of time corresponding to, for example, 2 R-R, is done until the appearance of, for example, the third R wave, and when such R wave appears (YES at step S74-7), the sequencer 5 returns the processing to the foregoing step S74-4. Accordingly, at a time when a specified delay time $T_{DL1}$ has passed from the reception of an ECG trigger signal synchronized with the peak value timing of the third R wave, scanning at the next slice encode amount SE2 starts in a similar manner to the foregoing one, so that echo signals are acquired from the three-dimensional imaging region Rima again (steps S74-4 and S74-5). Hereafter, the processing will be continued until echo signals at the last slice encode amount SEn (for instance, n=8) are acquired.

When the last scanning at the slice-encode amount SEn has been completed, the determination at step S74-6 becomes YES, the sequencer 5 informs the host computer 6 of the completion of the first-time (or second-time) imaging scan (steps S74-8). Then the processing is handed to the host computer 6.

According to the above procedures, the first-time (or second-time) imaging scan (imaging) employing the ECG synchronization technique is performed every a period of time of 2 R-R on the basis of, for example, 3D-FASE method.

Each echo signal emanated from the patient P is received by the RF coil 7 and sent to the receiver 8R, for each slice encode amount supplied by the slice gradient pulse $G_S$. The receiver 8R performs various types of pre-processing on the echo signal and converts it into digital amount of data. The digital echo data thus produced are sent to the calculation unit 10 through the sequencer 5, and mapped at given positions in a three-dimensional k-space formed by a memory, accordingly to the encoded amounts given to the echo signal.

Then, as shown in FIG. 2, after an appropriate interval of time, the second-time imaging scan (imaging) is carried out for the diastole in a similar way to the first-time imaging scan. In this second-time imaging scan, an optimum delay time $T_{DL2}$ to give a given time phase in the diastole predetermined through the foregoing ECG-prep scan is read (steps S70 and S71 in FIG. 16), then the ECG-synchronization is adopted using this delay time $T_{DL2}$ (step S74-4 in FIG. 17).

As a result, for this second-time imaging scan, as shown in FIGS. 18B and 18C, the scanning based on the three-dimensional FASE technique is performed at each phase encode amount SE at a synchronization timing delayed by a delay time of $T_{DL2}$ from an R-wave peak in the diastole. In this scan, the applied direction of the read-out gradient pulse $G_R$ is made to substantially agree with a moving direction of fluid to be imaged, such as blood flow. To the read-out gradient pulse $G_R$ are added the control pulses (dephasing pulses $P_{dephase}$ or rephasing pulses $P_{rephase}$) to control behaviors (dephasing or rephasing) of magnetic spins.

As a result, the second-time imaging scan is able to provide image data in the diastole, which are influenced by the spin control of either dephasing pulses $P_{dephase}$ or rephasing pulses $P_{rephase}$ added to the read-out gradient pulse $G_R$, similarly to the first-time imaging scan.

(2.2) Data Processing and Image Display

Figure 21:
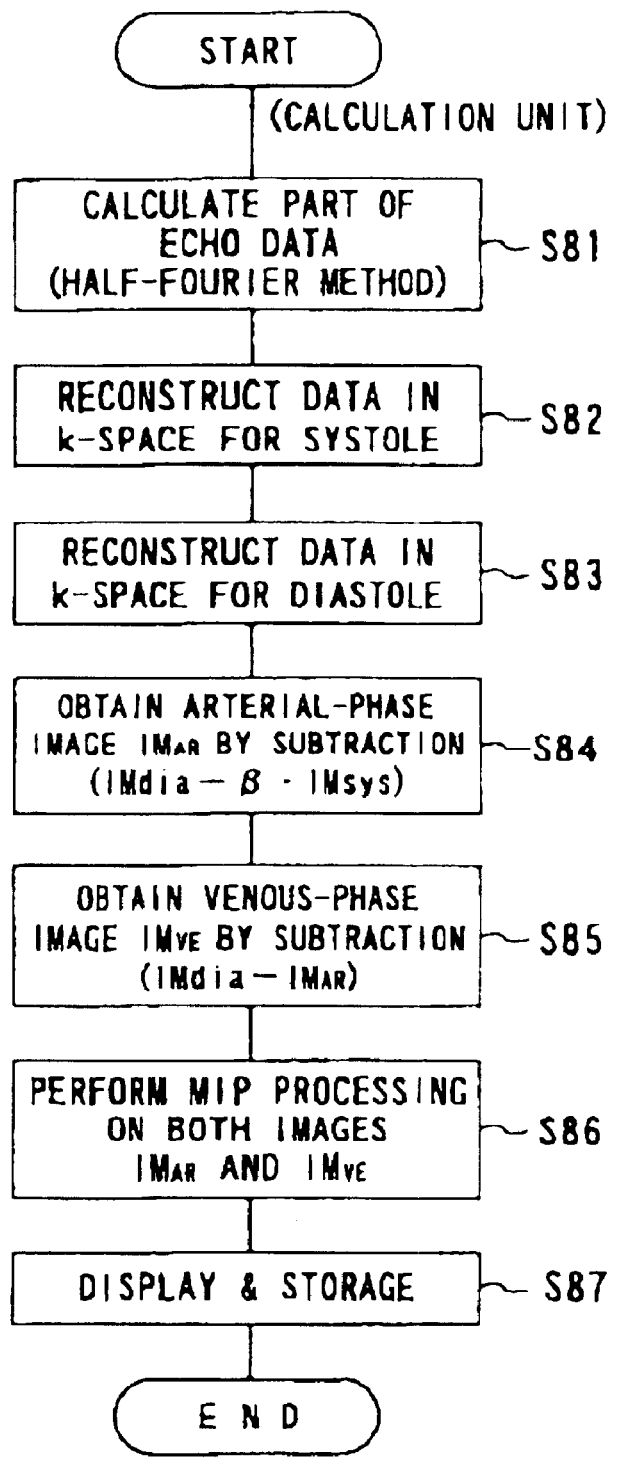
FIG. 21 is an outlined flowchart explaining echo data calculation and display processing in the second embodiment.

When the echo data acquisition has been finished, the host computer 6 obliges the calculation unit 10 to execute the processing shown in FIG. 21.

As shown therein, responsively to instructions from the host computer 6, the calculation unit 6 calculates echo data using the half Fourier technique from both of the systole-use k-space and the diastole-use k-space (step S81). That is, echo data that should be mapped in a remaining region of each k-space, but has been left with no data acquisition are calculated from the complex conjugate relationship, and mapped therein. This calculation completely fills up both k-spaces with echo data.

The calculation unit 10 reconstructs echo data in each of the k-paces for the systole and the diastole into image data through a three-dimensional Fourier transform, space by space (steps S82 and S83). Like the foregoing FIGS. 12A and 12B, obtained are three-dimensional image data at one time phase given by the delay time $T_{DL1}$ during the systole (systolic image $IM_{sys}$) and those at the other time phase given by the delay time $R_{DL2}$ during the diastole (diastolic image $IM_{dia}$).

A vein VE is only reflected in the systolic image $IM_{sys}$, but image data of an artery VR is hardly included in the systolic image $IM_{sys}$. On the other hand, in the diastolic image $IM_{dia}$, both of an artery AR and a vein VE are reflected, though degrees of the reflection are different from each other.

The principle of obtaining such systolic image $IM_{sys}$ and diastolic image $IM_{dia}$ will now be detailed in terms of the applied direction of the foregoing read-out gradient pulse $G_R$ and the function of the dephasing pulses $P_{dephase}$.

The phase of magnetic spins of an object, such as blood, that flows in the applied direction of the read-out gradient pulse makes it easier to be dephased more quickly on account of the dephasing pulses applied. In other words, to an object that is flowing, this is equivalent to the fact that the flow void effect provided from the flow itself is promoted. In contrast, the rephasing pulses give a rephasing function to the phase of magnetic spins of such blood flow.

For example, the inferior limb of an object to be examined will now be exemplified. In the case of the inferior limb, even if the artery is measured in the systole, its flow speed is slow and normally less than 1 cm/sec. Moreover, as for the vein measured in the systole and the artery and vein measured in the diastole, the blood moves at extremely slow speeds that can be regarded as if the blood is stationary. As shown in FIG. 18C, the read-out gradient pulse $G_R$ to which the dephasing pulses $P_{dephase}$ are added is applied to the inferior limb through the imaging scan (imaging) carried out at a desired time phase in each of the systole and the diastole.

Magnetic spins of the artery and vein are excited by those imaging scans to acquire echo signals. In this acquisition, flow speeds of the artery and vein differ from each other, although the difference might be rather small. Hence the difference in flow speed is reflected into promotion of a flow void effect based on the rephasing pulses, providing relative changes between intensities of echo signals.

To be specific, the systole will now be explained as follows. Since flowing at extremely slow speeds, the vein, when observed during the systole, is less in the flow void effect and depicted as bright blood with relative higher signal intensities, through it suffers a slight decrease in echo signal intensity due to the dephasing pulses. By contrast, the artery, when observed during the diastole, flows at larger speeds than those of the vein, so that the promotion of the flow void effect caused by the dephasing pulses is larger than that of the vein. This causes a larger decrease in the signal intensity of the artery, which depicts the artery as black blood. This state can be pictorially shown in a similar way to FIG. 12(a). In this figure, a hatching region shows the bright blood, while a dotted-line region shows the black blood.

On the other hand, since both artery and vein only move at extremely lower speeds during the diastole, they are depicted as bright blood, though they experience slight reductions in signal intensity because of the dephasing pulses. This condition is pictorially shown in a similar manner to FIG. 12(b).

Backing to the explanation of FIG. 21, in order to obtain an arterial phase image $IM_{AR}$, the calculation unit 10 performs a subtraction of "$IM_{dia} - \beta \cdot IM_{sys}$," pixel by pixel, using the systolic image $IM_{sys}$ and diastolic image $IM_{sys}$ (step S84). In the subtraction, $\beta$ is weighting factor. Similarly to FIG. 12(c) described before, setting the weighting factor to an appropriate value results in that image data of the vein VE becomes almost zero, providing three-dimensional image data of the arterial phase image $IM_{AR}$ in which only the artery AR is present.

Further, to obtain a venous phase image $IM_{VE}$, a subtraction of "$IM_{dia} - IM_{AR}$" is performed pixel by pixel (step S85). The image data $IM_{AR}$ has already been calculated by the foregoing weighed subtraction. In a similar way to FIG. 13, this second subtraction makes the image data of the artery AR substantially zero, providing three-dimensional image data of the venous phase image $IM_{VE}$ in which the vein VE is depicted alone. This second subtraction can be done with a weighted subtraction.

After the above subtractions, the calculation unit 10 proceeds to perform MIP (maximum intensity projection) processing for each of the arterial phase image $IM_{AR}$ and the venous phase image $IM_{VE}$. This produces data of a two-dimensional image (e.g., coronal image) obtained by observing, along a desired direction, blood vessels residing in each of the images (step S86).

Figure 22:
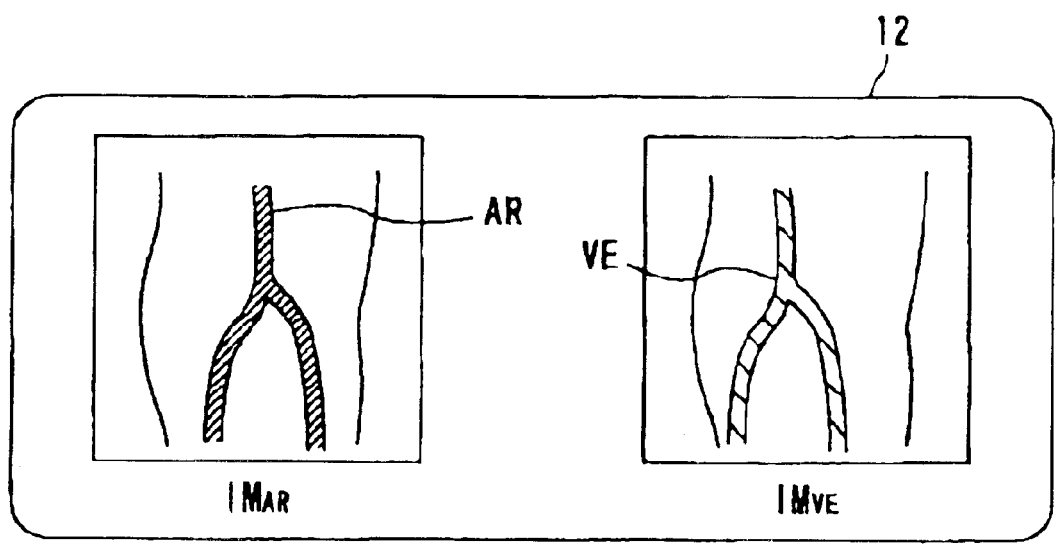
FIG. 22 exemplifies a state simultaneously displaying both of an arterial phase image and a venous phase image in the second embodiment.

The two-dimensional images $IM_{AR}$ and $IM_{VE}$ for the arterial and venous phases are displayed on the display unit 12 as shown in FIG. 22, for example, and those image data are stored in the storage unit 11 (step S87).

In addition to displaying the arterial and venous images $IM_{AR}$ and $IM_{VE}$, the systolic and diastolic images $IM_{sys}$ and $IM_{dia}$ may be displayed on the same screen to those for the arterial and venous images or on the screens of different monitors from the arterial and venous images.

(2.3) Advantages

As described, the MRI system of this embodiment employs the imaging in which the applied direction of the read-out gradient pulse $G_R$ is made to almost agree with a flow direction of fluid (such as blood) of which flow speed is lower, as can be observed in the inferior limb. Concurrently, the dephasing pulses $P_{dephase}$ or rephasing pulses $P_{rephase}$ are added to the read-out gradient pulse $G_R$.

Thus, the dephasing pulses $P_{dephase}$ or rephasing pulses $P_{rephase}$ are able to enhance relative differences of signal intensity between a first fluid that flows and a second fluid that flows at a slower speed than the first fluid. Therefore, even if blood vessels in the inferior limb, which are slower in flow speed than the abdomen and thorax, are imaged using, for example, the dephasing pulses, the relative differences of signal intensity are able to provide an image as shown in FIG. 22. As shown therein, the artery and vein are visualized in a mutually separated manner with higher depiction capability.

According the inventors' recognition, the above technique that the read-out gradient pulse is applied in the substantially same direction as the flow direction of fluid and the flow void effect is controlled by the positive use of dephasing and rephasing of magnetic spins has been newly developed. This technique can give relative differences to signal intensity between the artery and vein.

Additionally, in this embodiment, because the ECG-prep scan is used to previously determine the optimum ECG-synchronized timing for the systole and the diastole, blood flows targeted at each time phase during each of the systole and the diastole can be traced without fail. Previously conducted appropriate setting of the ECO-synchronized timing eliminates the necessity of repeating the same imaging. Operational work on operators and physical and mental burdens on patients are therefore reduced largely.

Further, it is possible to specify the slice or slice-encode direction in directions other than the superior-inferior direction of a patient, the entire scan time can be shortened, compared to imaging methods, such as the TOF technique, that require scanning to advance in the superior-inferior direction. This also lowers patient's burdens and increases throughput of patients.

It is unnecessary to inject a contrast medium into a patient, which leads to non-invasive imaging. This also remarkably reduces physical and mental burdens on patients. Also, troublesome operations inherent to the contrast technique, such as timing of a contrast effect should be measured, is also unnecessary. Differently from the contrast technique, the imaging technique according to the present embodiment can be repeated if necessary.

(Modifications of Second Embodiment)

The above embodiment uses both of the first-time and second-time imaging cans involving the read-out gradient pulse $G_R$ to which either of the dephasing pulses $P_{dephase}$ or the rephasing pulses $P_{rephase}$ are added (refer to FIGS. 18A to 18C).

As a modification of this embodiment, the dephasing pulses $P_{dephase}$ may be added in the first-time imaging scan conducted at a time phase during the diastole, as shown in FIG. 23A, while the rephasing pulses $P_{rephase}$ may be added in the second-time imaging scan conducted at a time phase during the systole, as shown in FIG. 23B.

In other words, between the systole and the diastole, the type of the control pulses to additionally control behaviors of magnetic spins is changed. This makes it possible to reflect the more effect of rephasing (i.e., flow compensation) in signal intensity in the diastole, thus increasing the signal intensity to improve a signal-to-noise ratio.

(Third Embodiment)

Referring to the foregoing figures and FIGS. 24 to 26, a third embodiment of the present invention will now be described. An MRI system used in this embodiment is configured in hardware in the same or similar way as or to the first and second embodiments.

In the third embodiment, the first-time and two-time imaging scans, that is, two times of imaging scans which have been conducted in the second embodiment are conducted as one-time imaging scan. In this scan, the foregoing dephasing and rephasing pulses are used according to the systole and diastole in each cardiac cycle.

The artery and vein in the inferior limb will now be employed as fluid of a slower speed and an artery/vein visually separated image thereof will now be obtained. Similarly to the sequence shown in FIG. 2, the ECG-prep scan is first performed, and then a one-time imaging scan is performed using the ECG-synchronized technique. The ECG-prep scan is conducted as described in the first and second embodiments, thereby delay times $T_{DL1}$ and $T_{DL2}$ measured from the R-waves being set so as to provide the highest depiction capability in each of the systole and diastole.

Then, the imaging scan is conducted in the form of a one-time imaging scan on the basis of the ECG-synchronized technique involving delay times $T_{DL1}$ and $T_{DL2}$. The procedures of this imaging scan, which are similar to those in FIGS. 24 and 25, are shown in FIG. 26 as its pulse sequence used for the scan.

(3.1) Imaging Scan

Figure 24:
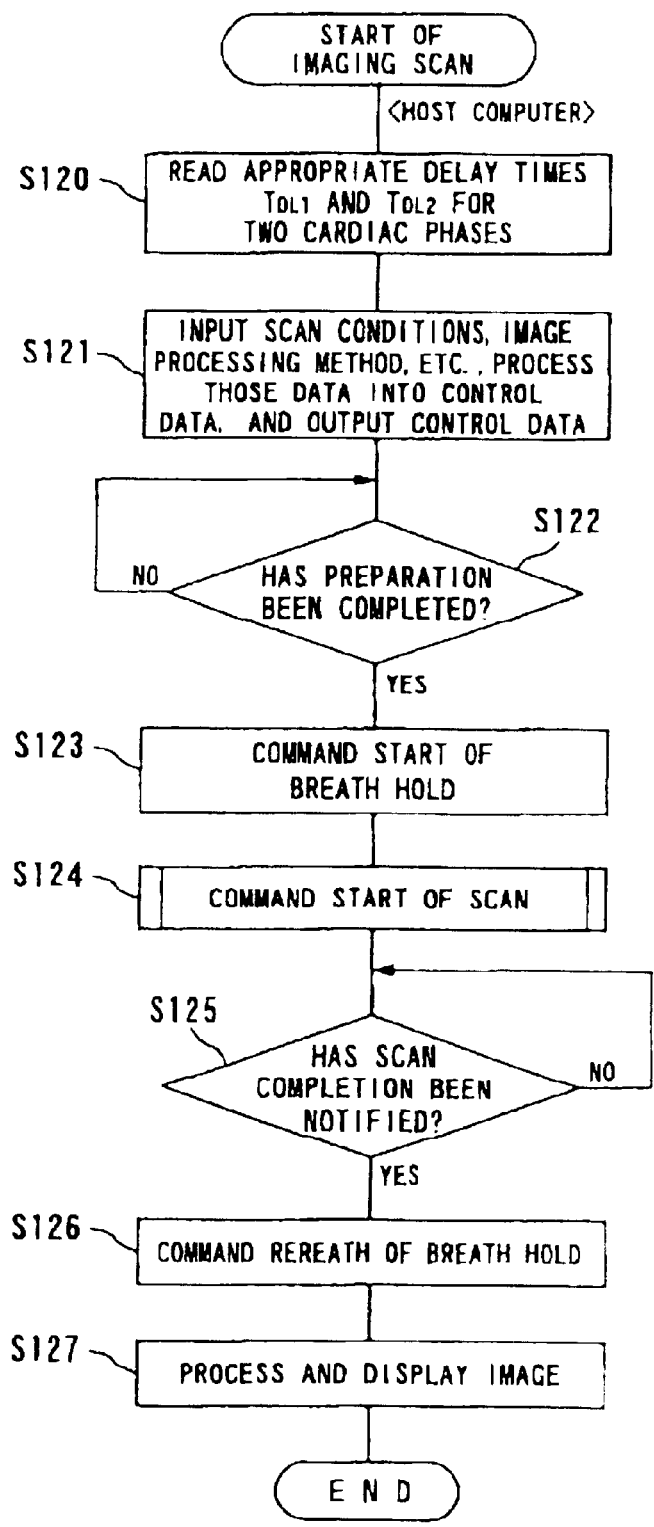
FIG. 24 is an outlined flowchart showing an imaging scan adopted by a third embodiment.
Figure 25:
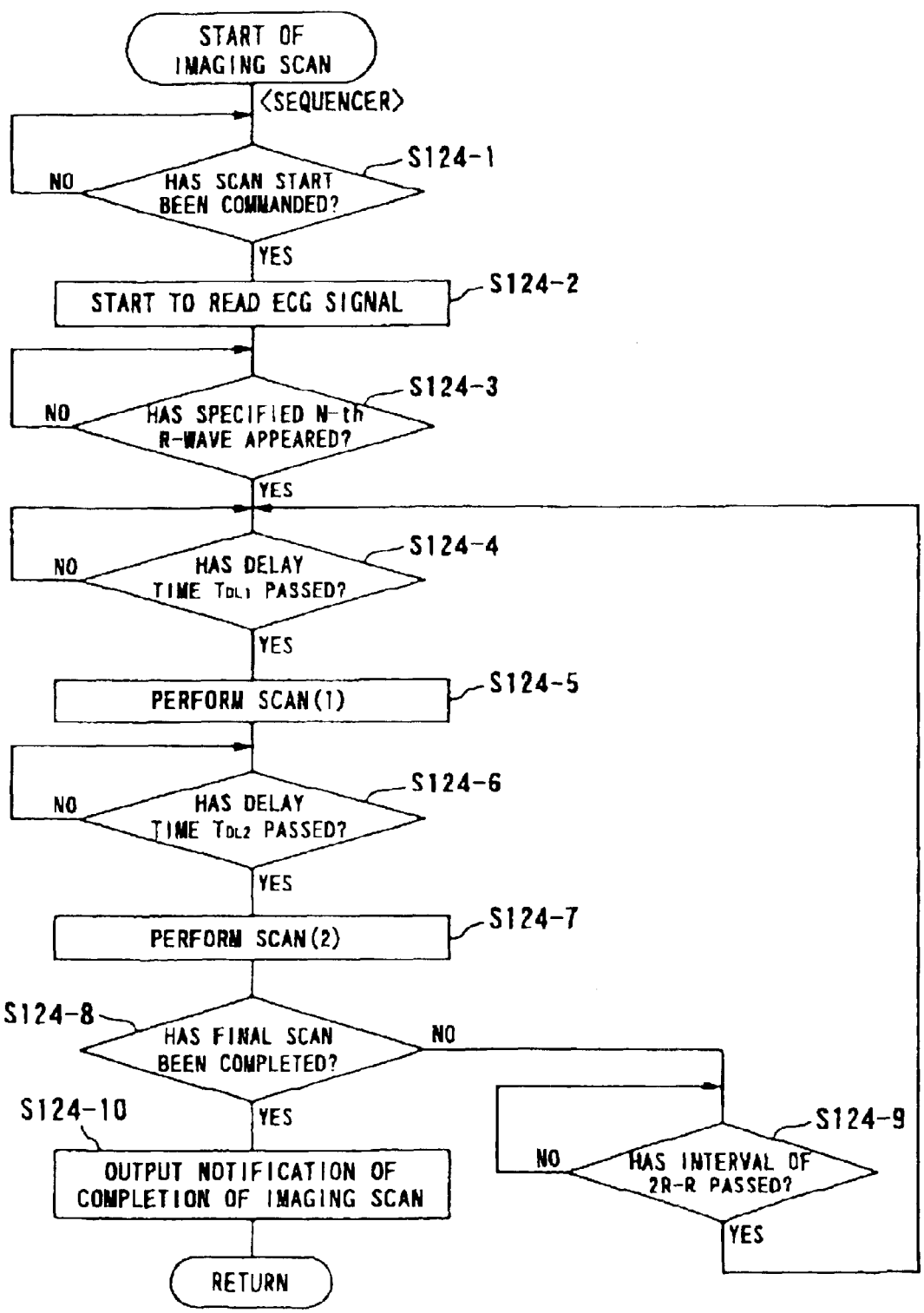
FIG. 25 is an outlined flowchart showing an imaging scan adopted by the third embodiment.

During performance of a not-shown main program, the host computer 6 also performs the processing shown in FIGS. 24 and 25 described before, as part of its duty, in response to operational information supplied from the input device 13.

Specifically, first of all, the host computer 6 reads two optimum delay times $T_{DL}$ via the input device 13, for example (step S120). The delay times $T_{DL}$, which are previously determined through the foregoing ECG-prep scan by an operator, are composed of an optimum delay time $T_{DL1}$ for the systole and an optimum delay time $T_{DL2}$ (>$T_{DL1}$) for the diastole, as described above. Information about those optimum delay times $T_{DL1}$ and $T_{DL2}$ may previously be determined and stored in, for example, the storage unit 11.

Then, the host computer 6 inputs information about scan conditions, an image processing method, and others, and process the information including the delay times $T_{DL1}$ and $T_{DL2}$ into control data. The control data are outputted to both of the sequencer 5 and the calculation unit 10 according to necessity (step S121).

It is then determined by the host computer 6 if the preparation before scanning has been completed or not in the similar manner to that in first embodiment. When completion of the preparation is determined, breath hold is instructed, then the imaging scan is instructed to start (steps S123 and S124).

On receiving instructions of starting the imaging scan (step S124-1 at FIG. 25), the sequencer 5 begins reading the ECG signal (step S124-2). Then the sequencer 5 detects the appearance of the peak value of the predetermined n-th R-wave (reference waveform) in the ECG signal, based on ECG trigger signals synchronized with their peak values (step S124-3).

When the appearance of the n-th R-wave is realized, the sequencer 5 waits for the delay time $T_{DL1}$ set to a specific time phase in the systole (step S124-4).

A time when the optimum delay time $T_{DL1}$ has passed is considered to be an optimum ECG-synchronized timing. Hence, the sequencer 5 begins to execute scanning for the systole at that time (step S124-5).

Specifically, according to information in relation to a pulse sequence memorized in advance, the transmitter 8T and gradient power supply 4 are driven. By this drive, a first scan $SN_{sys1}$ is performed based on the ECG-synchronized technique as shown in FIG. 26, at the first slice encode amount SE1 incorporated in a pulse sequence on the three-dimensional FASE method.

In this first san $SN_{sys1}$ the read-out gradient pulse $G_R$ applied to the patient's body axis direction substantially in parallel with the artery and vein in the patient's inferior limb. Additionally, dephasing pulses $P_{dephase}$ to dephase the phases of magnetic spins added to the temporal forward and backward parts of the read-out gradient pulse $G_R$ without temporal gaps. The echo train spacing used in this pulse sequence is shortened to approximately 5 msec.

Figure 26:
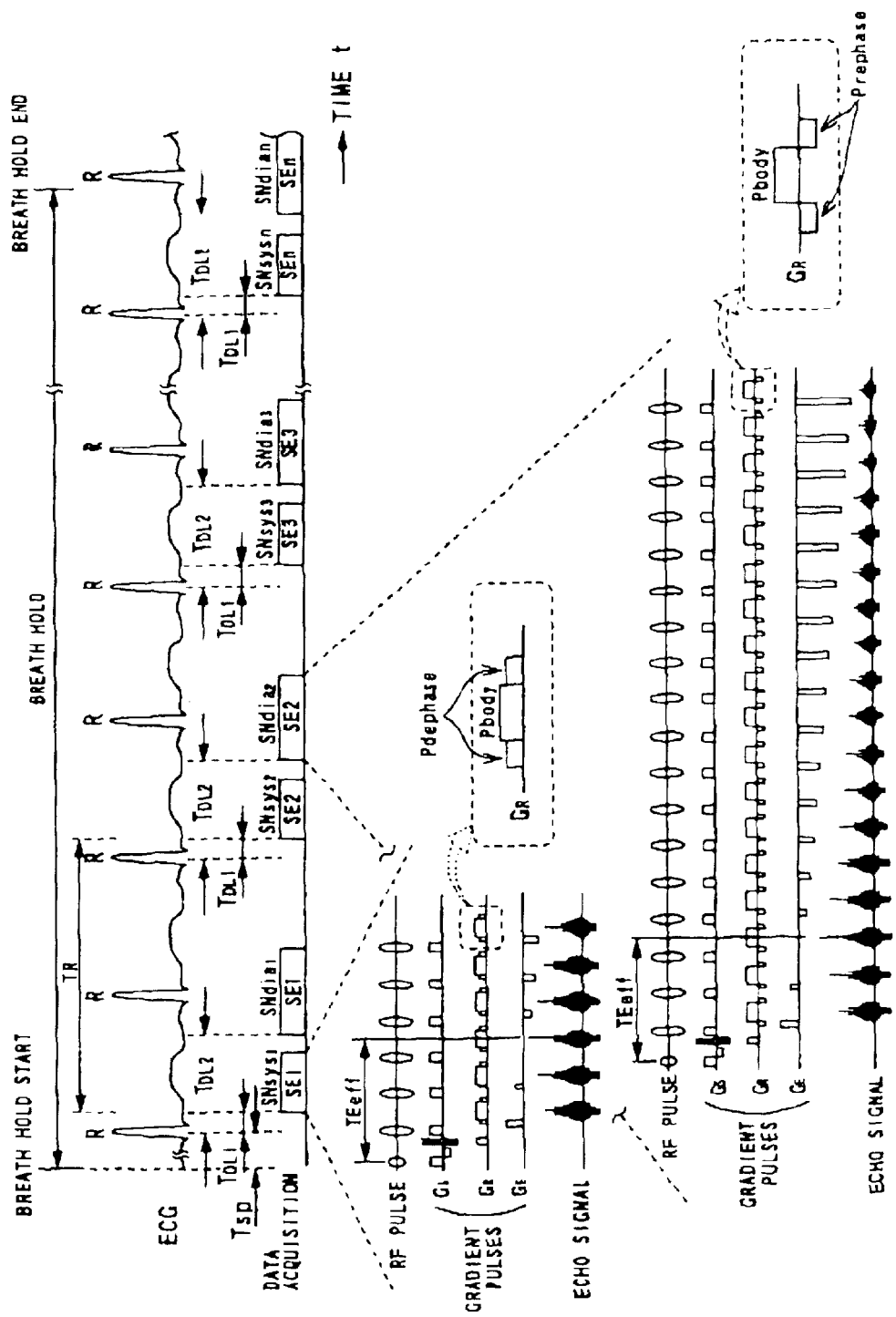
FIG. 26 is a timing chart exemplifying timing of the imaging scan carried out based on an electrocardiograph-synchronized technique in the third embodiment.

The pulse sequence used for the first scan $SN_{sysn}$ assigned to the systole adopts a less number of echoes that consecutively continue only during a shorter period of time after the start of the scan within one heartbeat, as shown in FIG. 26. The number of echoes is set, as pictorially shown in FIG. 9 described before, so that echo data to be mapped in only a central region (lower-frequency region) in the phase-encode direction ke of the k-space can be acquired every slice-encode amount. This setting allows a second scan $SN_{dian}$ for the diastole to start within the same heartbeat as the first scan $SN_{sysn}$ for the systole. Echo data that are short acquisition for a k-space $K_{sys}$ (a first k-space) for the systole are obtained by duplication of data from a k-space $K_{dia}$ (a second k-space) for the diastole later-explained and computation on the half Fourier technique.

Therefore, at the first slice-encode amount SE1, echo signals are acquired from a three-dimensional imaging region Rima (refer to FIG. 20) given to the inferior limb during a scan time of as shorter as about a few hundreds msec.

The sequencer 5 then proceeds to scan control for the diastole. Specifically, the sequencer 5 waits for the delay time $T_{DL2}$ set to a specific time phase during the diastole (step S124-6).

A time when the optimum delay time $T_{DL2}$ has passed is considered to be an optimum ECG-synchronized timing. Hence, the sequencer 5 executes a second scan for the diastole (step S124-7). Specifically, according to information in relation to a pulse sequence memorized in advance, the transmitter 8T and gradient power supply 4 are driven. By this drive, the first scan $SN_{dia1}$ is performed based on the ECG-synchronized technique as shown in FIG. 26, at the first slice encode amount SE1 incorporated in a pulse sequence on the three-dimensional FASE method.

In this second san $SN_{dia1}$, the read-out gradient pulse $G_R$ is also applied to the patient's body axis direction substantially in parallel with the artery and vein in the patient's inferior limb. Additionally, rephasing pulses $P_{rephase}$ to rephase the phases of magnetic spins added as shown to the temporal forward and backward parts of the read-out gradient pulse $G_R$ without temporal gaps. The echo train spacing used in this pulse sequence is also shortened to approximately 5 msec.

The pulse sequence used for the second scan $SN_{dian}$ assigned to the diastole is set, as shown in FIG. 26, to acquire echoes. The echoes are less in number than the echoes to be mapped into the entire k-space by the number of echoes thanks to using the half Fourier method, though the number of echoes is larger than that for the systole. Precisely, the number of echoes is determined so that echo data to be mapped in only a central region (lower-frequency region) and one outside region (higher-frequency region) next to the central region in the phase-encode direction ke of the k-space can be acquired every slice-encode amount. Echo data that are short acquisition for the k-space $K_{dia}$ for the diastole are obtained by computation on the half Fourier technique, as described later. The scan $SN_{dia1}$ for the diastole is carried out over the next heartbeat in usual cases, as shown in FIG. 26.

Therefore, at the first slice-encode amount SE1, echo signals are acquired from the three-dimensional imaging region Rima (refer to FIG. 20) given to the inferior limb during a scan time of about 600 msec.

When the first-time imaging scan is completed, the sequencer 5 determines whether or not the last scan has been completed (step S124-8). If determined to be NO (the last scan has not been ended yet), waiting will be continued, with the ECG signal monitored, until a predetermined shorter interval of time pass. This waiting permits the longitudinal magnetization of spins in stationary parenchyma to be positively suppressed from being restored (step S124-9). Such shorter interval of time for waiting is, for example, "2 R-R" from the R-wave used for the imaging scan.

For example, when the third R-wave measured with including that used to start the scanning appears after the waiting for an interval of, for instance, "2 R-R" (YES at step S124-9), the sequencer 5 proceeds to the processing at step S124-4.

Therefore, at a time when the delay time $T_{DL1}$ passes after the appearance of peak value of the third R-wave, the second-time first scan $SN_{sys2}$ for the systole is performed again at the next slice-encode amount SE2 in the similar manner to the last one. As a result, echo signals are acquired from the three-dimensional imaging region Rima (steps S124-4 and -5). Further, at another time when the delay time $T_{DL2}$ passes after the appearance of peak value of the third R-wave, the second-time second scan $SN_{dia2}$ for the diastole is performed again at the next slice-encode amount SE2 in the similar manner to the last one. As a result, echo signals are acquired from the three-dimensional imaging region Rima (steps S124-6 and S124-7).

Hereafter, echo signals are repeatedly acquired for each of the systole and diastole until the last slice-encode amount SEn (for example, n=8).

When the last scans $SN_{sysn}$ and $SN_{dian}$ at the slice-encode amount SEn have been completed, the determination at step S124-8 becomes YES, and the notification of completion of the imaging scans is issued from the sequencer 5 to the host computer 6 (step S124-10). Thus the processing returns to the host computer 6.

On receiving such notification from the sequencer 5 (step S125 in FIG. 24), the host computer 6 sends to the voice generator 16 a command to release the breath hold (step S126).

Accordingly, as pictorially shown in FIG. 26, during the one-time imaging scan (imaging), the ECG-synchronized scan for each of the systole and diastole is performed on, for example, the 3D-FASE technique with the n-piece slice-encode amounts, every "2 R-R," for instance.

The echo data acquired from the patient P are converted into digital echo data in a similar manner to the second embodiment. The echo data are sent to the calculation unit 10 via the sequencer 5, in which they are selectively mapped in three-dimensional systole-use and diastole-use k-spaces $K_{sys}$ and $K_{dia}$ both of which are formed by memories, correspondingly to each phase-encode amount and each slice-encode amount.

(3.2) Data Processing and Image Display

After the acquisition of the echo data, the host computer 6 instructs the calculation unit 10 to execute the processing shown in FIG. 11 described already.

As shown in FIG. 11, the calculation unit 6 responds to the instruction from the host computer 6 so as to complete entire mapping of data into the systole-use k-space $K_{sys}$ and the diastole-use k-space $K_{dia}$.

Then, the calculation unit 10 performs a three-dimensional Fourier transform on each of the k-spaces $K_{sys}$ and $K_{dia}$ for reconstructing images. As a result, as shown in FIGS. 12(a) and 12(b) described before, there are provided three-dimensional data of an image (systolic image) $IM_{sys}$ corresponding to the delay time $T_{DL1}$ in the systole and another image (diastolic image) corresponding to the delay time $T_{DL2}$ in the diastole. The data of the systolic image $IM_{sys}$ are formed with inclusion of only data of the vein VE, but almost no inclusion of data of the artery AR. On the other hand, through degrees of inclusion differ, the data of the diastolic image $IM_{dia}$ are formed with inclusion of both of the artery AR and vein VE.

Considering those facts, performed in turn by the calculation unit 10 are a subtraction of "$IM_{dia}-\beta \cdot IM_{sys}$" for producing an arterial phase image $IM_{AR}$, a subtraction of "$IM_{dia}-IM_{AR}$" for producing a venous phase image $IM_{VE}$, MIP (maximum intensity projection) processing for each of the arterial phase image $IM_{AR}$ and venous phase image $IM_{VE}$, two-dimensional display of the arterial phase and venous phase images, and storage of data of those images.

(3.3) Advantages

As described above, for performing the imaging scan with the MRI system of the present embodiment, the read-out gradient pulse $G_R$ is applied in a direction substantially in parallel with a flow direction of a blood vessel in the inferior limb. Concurrently, the dephasing pulses $P_{dephase}$ are added to the read-out gradient pulse $G_R$ applied during the systole, whilst the rephasing pulses $P_{rephase}$ are added to the read-out gradient pulse $G_R$ applied during the diastole.

Therefore, similarly to control of behaviors of magnetic spins described in the second embodiment, such addition is able to reduce signal intensity by promoting the flow void effect caused in blood flowing in the systole, in particular, in the artery. In contrast, such addition is able to give an effect of flow compensation to the vein and artery flowing in the diastole.

Hence, relative differences of signal intensity between blood that flows at a certain speed and blood that flows at a speed smaller than the certain speed can be made distinctly. So even if the blood vessels in the inferior limb are imaged, which are slower in flow speed than those in the abdomen and thorax, the artery and vein can be visually separated with clearness and displayed with higher depiction capability.

According to the MRI system of the present invention, the optimum scan start timing (delay time from the R-wave) is assigned to each of the systole and diastole in one cardiac cycle. Two shots of scans for the systole and diastole at one slice encode are performed in turn in the one time of imaging scan in an alternating fashion. Additionally, the scan for the systolic, which comes to first in one cardiac cycle, is shortened in time not to overlap with the following scan for the diastole by reducing its data acquisition time (corresponding to the number of echoes). The echo data acquired by such scan are mapped in the lower-frequency region of the k-space for the systole, such region being most significant in terms of improvement in the contrast of images. Short data in the k-space for the systole can be obtained by duplicating data acquired by the following scan for the diastole, which is capable of acquiring echoes over a relative longer period of time. The scans for the systole and diastole use the half Fourier technique to reduce the scan time as short as possible.

Thus, the two shots of scans for the systole and diastole at one slice-encode amount usually remain within an interval of about two heartbeats, Sequentially and alternately repeating such scans makes it possible to acquire echo data of blood flow for the systole and diastole during a breath hold duration of one time. Namely, three-dimensional image data of blood flow for each of the systole and diastole are acquired at its optimum timing through one time of imaging.

There is therefore no need to perform each imaging scan for each of the systole and diastole (that is, in total, two times of imaging), but only one time of imaging is enough. Hence, the imaging time is lessened largely and throughput of patients is improved. Particularly, a reduction in the imaging time becomes noticeable when three-dimensional imaging is carried out. Further, misregistration due to patient's motions can also be reduced greatly, thereby improving image quality. Artery-phase/venous-phase visually separated blood flow images (MRA images) can be obtained from echo data at acquired by one time of imaging, so the imaging is excellent in efficiency. The other operations and advantages obtained in the second embodiment are also available to this third embodiment.

(Modifications of Third Embodiment)

In the foregoing third embodiment, the first-time and second-time imaging scans use, as shown in FIG. 26, the dephasing pulses added to the read-out gradient pulse for the systole and the rephasing pulses added to the read-out gradient pulse for the diastole. Alternatively, only the dephasing pulses may be added to the read-out gradient pulse for both of the systole and the diastole. This addition is able to reflect, into signal intensity, promoted states of the flow void effect due to blood flow speeds different at each time phase, in the similar way to the second embodiment (refer to FIGS. 18A to 18C). Hence, the artery and vein can be visually separated with precision.

(Modifications Common to First to Third Embodiments)

The first to third embodiments can be practiced in other various modified forms

For instance, the foregoing embodiments are configured to present both of the arterial phase and venous phase images, but only the arterial phase image may be produced by a subtraction and displayed. In this case, the step S36 in the processing of FIG. 11, that is, the subtraction for the venous phase image, can be omitted. Alternatively, only the arterial phase image may be displayed, though the subtraction is done for both of the arterial phase image and the venous phase image.

In the foregoing embodiments, the half Fourier technique is used for each scan for each of the systole and diastole, the half Fourier technique may be replaced by other techniques. In that case, one preferred example is that the scan for the diastole acquires echo data that can be mapped in the entire k-space and echo data present in both ended regions (high-frequency regions) are individually duplicated into corresponding regions of the k-space for the systole.

Moreover, the foregoing embodiments have been described using the three-dimensional scan. Instead, the two-dimensional scan can be applied to the embodiments similarly. The pulse sequence to be used is not limited to the FASE technique itself, but pulse sequences based on an FSE technique using an inversion recovery (IR) pulse or an FASE technique modified to use the inversion recovery pulse can be available.

The post-processing of echo data in the foregoing embodiments is configured such that echo data are once converted into image data in the actual space, and then the image data undergo the subtractions to obtain the arterial phase image and venous phase image. Instead of this, the subtractions may be conducted with echo data mapped in the k-spaces $K_{sys}$ and $K_{dia}$, as long as their matrix sizes are equal to each other. The subtracted echo data are then reconstructed into a blood flow image.

Further, as to the configuration to detect a signal indicative of heartbeats of an object to be imaged, the foregoing configuration detecting the ECG signal may be replaced by a PPG (peripheral gating) detector to detect a pulse wave on a finger using an optical signal.

Furthermore, in the MRI system according to each of the foregoing embodiments and modifications, image data at the two time phases are formed into one set of image data, but the present invention is not limited to this mode. For instance, the read-out gradient pulse to which the dephasing pulses or rephasing pulses are added is set so that it is applied almost in parallel with a flow direction of fluid (blood, lymph, or others). Then, an imaging scan using the read-out gradient pulse is performed one time to obtain a single image, with no relation to the cardiac time phases. The fluid is imaged in bright or black into this image, with degrees of promotion of the flow void effect in the fluid reflected. Therefore, this image also provides flow information about the fluid.

As another modification, means for controlling the intensities of the foregoing dephasing pulses and rephasing pulses according to flow speeds of fluid to be imaged can be provided. This means is composed of, for example, the input device 13, host computer 6, and/or storage unit 11. In response to information indicative of both of a region to be imaged and fluid to be imaged, which is provided by an operator via the input device 13, the host computer 6 refers to a memory table previously stored in the storage unit 11. The table memorizes pulse intensities fluid by fluid. The host computer 6 provides the sequencer 5 with the intensity of a dephasing pulse or rephasing pulse according to the reference result. Alternatively, an operator is also able to use input device 13 for directly giving the system desired pulse intensity.

Though the embodiments have been described above, the present invention is not restricted to the configurations described in the embodiments, and various modifications and adaptations will be readily apparent to those skilled in the art without departing from the substance of scope of the present invention. Those modifications and adaptations should be construed as being included into the present invention.

What is claimed is:

1. An MRI system for obtaining an image relating to fluid within a region to be imaged of an object, comprising:
a time phase setting unit configured to set two different cardiac time phases falling into a systole and a diastole of a cardiac cycle of the object;
a scanning unit configured to perform, toward the region to be imaged of the object, an MR imaging scan starting in turn at each of the two cardiac time pahses set by the time phase setting unit to acquire two sets of echo data, the MR imaging scan comprising a first scan starting at one of the two cardiac time phases falling in the systole and a second scan starting at the other of the two cardiac time phases falling in the diastole, both the first scan and the second scan being based on a half-Fourier technique; and
an image producing unit configured to produce, from the two sets of echo data acquired by the scanning unit, the image relating to the fluid.

2. The MRI system of claim 1, wherein the scanning unit is configured to perform both the first and second scans, respectively, on either the same slice of the region or a volume of the region specified by each slice encodes.

3. The MRI system of claim 1, wherein the first scan is is carried out using a pulse sequence generating an echo signal to map echo data in a central region of a first k-space for producing the image, the central region corresponding to a lower-frequency region in a phase-encode direction of the first k-space, and the second scan is carried out using a pulse sequence generating an echo signal to map echo data in both a central region and one of both end regions other than the central region of a second k-space for producing the image, the central region corresponding to a lower-frequency region in a phase-encode direction of the second k-space and both of the end regions corresponding to a higher-frequency region in the phase-encode direction of the second k-space.

4. The MRI system of claim 3, wherein the image producing unit includes duplicating means for duplicating echo data existing in one end region of the second k-space to one of both end regions of the first k-space, the one end region of the first k-space being yet to be mapped with echo data, and calculating means for calculating, with regard to each of the first and second k-spaces, additional echo data based on the half-Fourier technique so that the calculated additional echo data is mapped into the remaining end region being yet to be mapped.

5. The MRI system of claim 4, wherein the image producing means includes arterial phase image producing means for obtaining one of echo data and image data representing an arterial phase image through a predetermined type of calculation executed between one of echo data of the first k-space and image data thereof and one of echo data of the second k-space and image data thereof.

6. The MRI system of claim 5, wherein the predetermined type of calculation executed by the arterial phase image producing means is one of subtraction, weighted difference calculation, and addition.

7. The MRI system of claim 5, wherein the image producing unit includes venous phase image producing means for obtaining one of echo data and image data thereof representing a venous phase image by executing subtraction between one of echo data of image data representing the arterial phase image obtained by the arterial phase image producing means and one of echo data of the second k-space and image data thereof.

8. The MRI system of claim 1, wherein each of the first and second scans is either one of a two-dimensional scan and a three-dimensional scan.

9. The MRI system of claim 1, wherein the unit is configured to execute the MR imaging scan with a pulse sequence based on one of an EPI (Echo Planar Imaging) technique and an FSE (Fast Spin Echo) technique.

10. The MRI system of claim 1, wherein the time phase setting unit has detecting means for detecting a signal indicative of the cardiac time phases of the object, preparing means for obtaining a plurality of MR images by executing a preparing MR sequence a plurality of times toward the region to be imaged of the object at different timings from a heartbeat reference wave appearing cyclically in the signal detected by the detecting means, and means for determining the two cardiac time phases from the plurality of MR images obtained by the preparing means.

11. The MRI system of claim 10, wherein the signal indicative of the cardiac time phases is an ECG signal of the object and the heartbeat reference wave is an R-wave of the ECG signal.

12. The MM system of claim 1, wherein the scanning unit is configured to execute a pulse sequence including readout gradient pulse of which applied direction is substantially in accordance with a moving direction of the fluid.

13. The MM system of claim 12, wherein the readout gradient pulse has a main pulse for reading out the echo signal and a control pulse for controlling behaviors of magnetic spins of the fluid concerning a phase of the magnetic spins, the control pulse being added to the main pulse on a time axis thereof.

14. The MM system of claim 13, wherein the control pulse is a pulse responsible for at least one of dephasing and rephasing of the magnetic spins.

15. The MRI system of claim 13, further comprising a unit configured to control an intensity of the control pulse in accord with a flow velocity of the fluid.

16. An MR imaging method of obtaining an image relating to fluid within a region to be imaged of an object, comprising:

setting two different cardiac time phases falling into a systole and a diastole of a cardiac cycle of the object;

performing toward the region to be imaged of the object, an MR imaging scan starting in turn at each of the two cardiac time phases to acquire two sets of echo data, the MR imaging scan comprising a first scan starting at one of the two cardiac time phases falling in the systole and a second scan starting at the other of the two cardiac time phases falling in the diastole, both of the first scan and the second scan being based on a half-Fourier technique; and producing, from the two sets of acquired echo data, the image relating to the fluid.

17. An MRI system for obtaining an image relating to fluid within an object, in which the object placed in a static magnetic field is subjected to a scan based on a pulse sequence including a readout gradient pulse, comprising:

a time phase setting unit configured to set a cardiac time phase of the object;

a scanning unit configured to perform the scan at the cardiac time phase to acquire an echo signal from the object under a condition that an applied direction of the readout gradient pulse is substantially in accordance with a moving direction of the fluid in motion within the object; and an image producing unit configured to produce, from the echo signal, the image relating to the fluid, wherein the readout gradient pulse has a main pulse for reading out the echo signal and a control pulse for controlling behaviors of magnetic spins of the fluid concerning a phase of the magnetic spins, the control pulse being added to the main pulse along a time axis of the main pulse.

18. The MRI system of claim 17, wherein the control pulse is a pulse responsible for at least one of dephasing and rephasing of the magnetic spins.

19. The MRI system of claim 18, wherein the readout gradient pulse has a main pulse for reading out the echo signal and a control pulse for controlling behaviors of magnetic spins of the fluid concerning a phase of the magnetic spins, the control pulse being added to the main pulse along a time axis of the main pulse.

20. The MRI system of claim 19, wherein the control pulse is a pulse responsible for at least one of dephasing and rephasing of the magnetic spins.

21. The MRI system of claim 20, wherein the control pulse belonging to the readout gradient pulse in the pulse sequence used for each of the first and second scans is formed as a pulse responsible for at least one of the dephasing and rephasing.

22. The MRI system of claim 20, wherein the control pulse belonging to the readout gradient pulse in the pulse sequence used for the first scan executed at one of the two cardiac time phases is formed as a pulse responsible for the dephasing and the control pulse belonging to the readout gradient pulse in the pulse sequence used for the second scan executed at the other cardiac time phase is formed as a pulse responsible for the rephasing.

23. The MRI system of claim 22, wherein the time phase setting is configured to set the one cardiac time phase falling into a diastole of the object and set the other cardiac time phase falling into a systole of the object.

24. The MRI system of claim 19, wherein the control pulse is changeable in a wave area thereof.

25. The MRI system of claim 17, comprising a unit for controlling an intensity of the control pulse in accord with a flow velocity of the fluid.

26. An MRI system for obtaining an image relating to fluid within an object, in which the object placed in a static magnetic field is subjected to a scan based on a pulse sequence including a readout gradient pulse, comprising:
 a time phase setting unit configured to set a cardiac time phase of the object;
 a scanning unit configured to perform the scan at the cardiac time phase to acquire an echo signal from the object under a condition that an applied direction of the readout gradient pulse is substantially in accordance with a moving direction of the fluid in motion within the object; and
 an image producing unit configured to produce, from the echo signal, the image relating to the fluid,
 wherein the time phase setting unit is configured to set two cardiac time phases of the object,
 the scanning unit is configured to acquire data comprising two sets of echo signals by applying first and second scans to the object at the two cardiac time phases, respectively; and
 the image producing unit is configured to produce an image of the fluid from the data.

27. The MRI system of claim 26, wherein the scanning unit is configured to sequentially perform the first and second scans on either the same slice of the region or volume of the region specified by each slice encode during one time of imaging for the object.

28. The MRI system of claim 26, wherein the fluid is a blood flow within the object.

29. The MRI system of claim 28, wherein the blood flow consists of an artery and a vein slowly flowing in an inferior limb of the object, and
 the image producing unit has artery/vein image producing means that produces images in which the artery and vein are visually separated from each other.

30. The MRI system of claim 26, wherein each of the first and second scans is formed based on a half-Fourier technique.

31. The MRI system of claim 30, wherein the first scan carried out using a pulse sequence generating an echo signal to map echo data in a central region of a first k-space for producing the image, the central region corresponding to a lower-frequency region in a phase-encode direction of the first k-space, and
 the second scan is carried out using a pulse sequence generating an echo signal to map echo data in both of a central region and one of both end regions other than the central region of a second k-space for producing the image, the central region corresponding to a lower-frequency region in a phase-encode direction of the second k-space and both of the end regions corresponding to a higher-frequency region in the phase-encode direction of the second k-space.

32. The MRI system of claim 31, wherein the image producing unit has duplicating means for duplicating echo data existing in the one end region of the second k-space to on of both end regions of the first k-space, the one end region of the first k-space being yet to be mapped with echo data, and calculating means for calculating, in each of the first and second k-spaces, additional echo data based on the half-Fourier technique so that the calculated additional echo data is mapped into the remaining end region being yet to be mapped.

33. The MRI system of claim 32, wherein the image producing unit includes arterial phase image producing means for obtaining one of echo data and image data representing an arterial phase image through a predetermined type of calculation executed between one of echo data of the first k-space and image data thereof and one of echo data of the second k-space and image data thereof.

34. The MRI system of claim 33, wherein the predetermined type of calculation executed by the arterial phase image producing means is one of subtraction, weighted difference calculation, and addition.

35. The MRI system of claim 33, wherein the image producing unit includes venous phase image producing means for obtaining one of echo data and image data thereof representing a venous phase image by executing subtraction between one of echo data of image data representing the arterial phase image obtained by the arterial phase image producing means and one of echo data of the second k-space and image data thereof.

36. The MRI system of claim 30, wherein each of the first and second scans is either one of a two-dimensional scan and a three-dimensional scan.

37. The MRI system of claim 30, wherein the time phase setting unit has detecting means for detecting a signal indicative of the cardiac time phases of the object, preparing means for obtaining a plurality of MR images by executing a preparing MR sequence a plurality of times toward the region to be imaged of the object at different timings from a heartbeat reference wave appearing cyclically in the signal detected by the detecting means, and means for determining the two cardiac time phases from the plurality of MR images obtained by the preparing means.

38. The MRI system of claim 37, wherein the signal indicative of the cardiac time phases is either an EGG signal or a PPG signal of the object and the heartbeat reference wave is an R-wave of either of the ECG signal or the PPG signal.

39. The MRI system of claim 26, wherein the pulse sequence used by each of the first and second scans is composed of a train of pulses based on one of a FASE (Fast Asymmetric SE) technique, EPI (Echo Planar Imaging) technique, FSE (Fast Spin Echo) technique, and SE (Spin Echo) technique.

40. An MR imaging method of obtaining an image relating to fluid within a region to be imaged of an object, comprising:
 setting a cardiac time phase of an object;
 performing, toward the region to be imaged of the object, a scan at the cardiac time phase with use of a pulse sequence including a readout gradient pulse of which applied direction is substantially in accordance with a moving direction of fluid in motion within the object, so that an echo signal is acquired; and producing, from the echo signal, the image relating to the fluid, wherein the readout gradient pulse has a main pulse to read out the echo signal and at least one of a dephase pulse and a rephase pulse responsible for dephasing and rephasing phases of magnetic spins of the fluid, respectively, the at least one pulse being added to the main pulse along a time axis of the main pulse.

41. An MRI system for obtaining an image relating to fluid within a region to be imaged of an object, comprising:

a magnet for generating a static magnetic field in which an object is placed;

an RF coil device through which an RF magnetic field is transmitted to the object and an echo signal emanated from the object is received;

a transmitter for transmitting the RF magnetic field to the object through the RF coil device, the RF magnetic field being based on a pulse sequence;

a gradient power supply for applying a gradient based on the pulse sequence to the object through a gradient coil;

a receiver for receiving the echo signal through the RF coil device, the echo signal being generated in response to performance of the pulse sequence;

a calculating unit for producing the echo signal received by the receiver into the image; and a controller for controlling operations of the transmitter, receiver and gradient power supply in conformity with the pulse sequence, wherein the controller controls the operations of transmitter, receiver and gradient power supply so that two different cardiac time phases falling into a systole and a diastole of a cardiac cycle of the object are set, and, as the pulse sequence, an imaging scan is executed in synchronism with each of the two different cardiac time phases in turn to acquire two sets of the echo signal, the imaging scan comprising a first scan starting at one of the two cardiac time phases falling in the systole and a second scan starting at the other of the two cardiac time phases falling in the diastole, both of the first scan and the second scan being based on a half-Fourier technique, and the calculating unit produces the image relating to the fluid within the region to be imaged of the object from the two sets of the echo signal acquired correspondingly to each of the two different cardiac time phases.

42. An MRI system for obtaining an image relating to fluid within a region to be imaged of an object, comprising:

a magnet for generating a static magnetic field in which an object is placed;

an RF coil device through which an RF magnetic field is transmitted to the object and an echo signal emanated from the object is received;

a transmitter for transmitting the RF magnetic field to the object through the RF coil device, the RF magnetic field being based on a pulse sequence;

a gradient power supply for applying a gradient based on the pulse sequence to the object through a gradient coil;

a receiver for receiving the echo signal through the RF coil device, the echo signal being generated in response to performance of the pulse sequence;

a calculating unit for producing the echo signal received by the receiver into the image; and a controller for controlling operations of the transmitter, receiver and gradient power supply in conformity with the pulse sequence, wherein the controller controls the operations of transmitter, receiver and gradient power supply so that a cardiac time phase of the object is set and, as the pulse sequence, a pulse sequence for an imaging scan is executed in synchronism with the cardiac time phase, the imaging-scan pulse sequence including a readout gradient pulse of which applied direction being substantially in accordance with a moving direction of fluid in motion within the object, the calculating unit produces the image relating to the fluid within the object from the echo signal acquired through the receiver correspondingly to performance of the imaging-scan pulse sequence, and wherein the readout gradient pulse has a main pulse to read out the echo signal and a control pulse to control behaviors of magnetic spins of the fluid concerning a phase of the magnetic spins, the control pulse being added to the main pulse along a time axis of the main pulse.

43. The MRI system of claim 42, wherein the control pulse is formed into a pulse responsible fore at least one of dephasing and rephasing the magnetic spins.

44. The MRI system of claim 43, wherein the cardiac time phase comprises two cardiac time phases falling into a systole and a diastole of the object, respectively, and the imaging scan consists of a first scan and a second scan made to start at the two cardiac time phases, respectively.

45. An MRI system for obtaining an image relating to fluid within a region to be imaged of an object, comprising:

time phase setting means for setting two different cardiac time phases falling into a systole and a diastole of a cardiac cycle of the object;

scanning means for performing, toward the region to be imaged of the object, an MR imaging scan starting in turn at each of the two cardiac time phases set by the time phase setting means to acquire two sets of echo data, the MR imaging scan comprising a first scan starting at one of the two cardiac time phases falling in the systole and a second scan starting at the other of the two cardiac time phases falling in the diastole, both the first scan and the second scan being based on a half-Fourier technique; and image producing means for producing, from the two sets of echo data acquired by the scanning means, the image relating to the fluid.

* * * * *